(12) United States Patent
Livney et al.

(10) Patent No.: US 9,005,664 B2
(45) Date of Patent: Apr. 14, 2015

(54) DENATURED LACTOGLOBULIN AND POLYPHENOL COASSEMBLIES

(75) Inventors: Yoav D. Livney, Misgav (IL); Avi Shpigelman, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 13/275,223

(22) Filed: Oct. 17, 2011

(65) Prior Publication Data

US 2012/0093933 A1   Apr. 19, 2012

Related U.S. Application Data

(60) Provisional application No. 61/393,901, filed on Oct. 17, 2010.

(51) Int. Cl.
| | |
|---|---|
| *A61K 9/14* | (2006.01) |
| *A61K 9/00* | (2006.01) |
| *A61P 3/04* | (2006.01) |
| *A61P 9/00* | (2006.01) |
| *A61P 3/00* | (2006.01) |
| *A61K 31/353* | (2006.01) |
| *A61P 25/28* | (2006.01) |
| *B82Y 5/00* | (2011.01) |
| *C07K 14/47* | (2006.01) |
| *A23L 1/30* | (2006.01) |
| *A23L 1/00* | (2006.01) |
| *A61K 9/10* | (2006.01) |
| *A61K 9/19* | (2006.01) |
| *A61K 9/51* | (2006.01) |

(52) U.S. Cl.
CPC .............. *C07K 14/4717* (2013.01); *B82Y 5/00* (2013.01); *A23L 1/3002* (2013.01); *A23L 1/0029* (2013.01); *A61K 9/0095* (2013.01); *A61K 9/10* (2013.01); *A61K 31/353* (2013.01); *A61K 9/19* (2013.01); *A61K 9/5169* (2013.01); *Y10S 977/773* (2013.01); *Y10S 977/882* (2013.01)

(58) Field of Classification Search
None
See application file for complete search history.

(56) References Cited

U.S. PATENT DOCUMENTS

| | | | |
|---|---|---|---|
| 3,958,581 A | 5/1976 | Abegg | |
| 3,962,418 A | 6/1976 | Birkofer | |
| 6,190,591 B1 | 2/2001 | Van Lengerich | |
| 6,290,974 B1 | 9/2001 | Swaisgood | |
| 6,428,814 B1 * | 8/2002 | Bosch et al. | 424/501 |

(Continued)

FOREIGN PATENT DOCUMENTS

| | | |
|---|---|---|
| JP | 2005-124554 | 5/2005 |
| WO | 2007/122613 | 11/2007 |
| WO | 2009/130704 A1 | 10/2009 |

OTHER PUBLICATIONS

Ru et al. "Encapsulation of epigallocatechin-3-gallate (EGCG) using oil-in-water (O/W) submicrometer emulsions stabilized by I-carrageenan and β-lactoglobulin", J Agric Food Chem. Oct. 13, 2010; 58(19):10373-81 (p. 10375).*

(Continued)

*Primary Examiner* — Ernst V Arnold
*Assistant Examiner* — Jianfeng Song
(74) *Attorney, Agent, or Firm* — Browdy and Neimark, PLLC

(57) ABSTRACT

The present invention is directed to co-assembled nanoparticle composition comprising denatured β-lactoglobulin and at least one nutraceutical compound, specifically polyphenols, such as EGCG, compositions comprising same and methods of preparing thereof.

13 Claims, 15 Drawing Sheets

(56) References Cited

U.S. PATENT DOCUMENTS

| | | | |
|---|---|---|---|
| 6,528,497 | B1 | 3/2003 | Basten |
| 2003/0185960 | A1 | 10/2003 | Augustin |
| 2005/0170062 | A1* | 8/2005 | Burling et al. ............... 426/601 |
| 2006/0134282 | A1 | 6/2006 | Mellema |
| 2007/0085058 | A1* | 4/2007 | Mora-Gutierrez et al. ............... 252/400.21 |
| 2007/0231453 | A1* | 10/2007 | Bovetto et al. ............... 426/656 |
| 2009/0035437 | A1* | 2/2009 | Bovetto et al. ............... 426/588 |
| 2010/0159105 | A1 | 6/2010 | Zhu |
| 2011/0038987 | A1 | 2/2011 | Danino |

OTHER PUBLICATIONS

Riihimäki et al. "Binding of Phenolic Compounds and Their Derivatives to Bovine and Reindeer β-Lactoglobulin", J. Agric. Food Chem. 2008, 56, 7721-7729 (p. 7721).*

Zimet et al. "Beta-Lactoglobulin and its nanocomplex with pectin as vehicles for ω-3 polyunsaturated fatty acids", Food Hydrocoloids 23 (Jun. 2009), 1120-1126 (p. 1120).*

Chen et al. "Chitosan / β-lactoglobulin core-shell nanoparticles as nutraceutical carriers", Biomaterials 26 (2005) 6041-6053 (whole document).*

Boger, "The pharmacodynamics of L-Arginie", The Journal of Nutrition, 137, 2007, 1650S-1655S (p. 1650s).*

Chu et al. "Preparation of Protein-stabilized β-Carotene Nanodispersions by Emulsification-Evaporation Method", J. Am. Oil Chem. Soc., Oct. 2007, 1053-1062.*

Riihimäki et al. "Binding of Phenolic Compounds and Their Derivatives to Bovine and Reindeer β-Lactoglobulin", J. Agric. Food Chem. 2008, 56, 7721-7729.*

Almajano et al., "Changes in the antioxidant properties of protein solutions in the presence of epigallocatechin gallate", Food Chemistry, 101, 2007, 126-130.*

Chen, L. and Subirade, M. (2005) Chitosan/beta-lactoglobulin core-shell nanoparticles as nutraceutical carriers. Biomaterials 26(30):6041-6053.

Liang, Li et al., (2008) Interaction of beta-Lactoglobulin with resveratrol and its biological implications. Biomacromolecules 9(1):50-56 Epub Dec. 8, 2007.

Livney, Yoav D. et al., (2003) Steric Effects Governing Disulfide Bond Interchange during Thermal Aggregation in Solutions of b-Lactoglobulin B and a-Lactalbumin. J Agric Food Chem 51(27):8098-8106. Epub Dec. 3, 2003.

Mizooku, Yasuo et al., (2003) Analysis of oxidized epigallocatechin gallate by liquid chromatography/mass spectrometry. Rapid Communications in Mass Spectrometry 17(16):1915-1918 Epub Jul. 13, 2003.

Riihimaki, Laura H. et al., (2008) Binding of phenolic compounds and their derivatives to bovine and reindeer beta-lactoglobulin. J Agric Food Chem 56(17):7721-7729.

Shpigelman, Avi et al., (2010) Thermally-induced protein—polyphenol co-assemblies: beta lactoglobulin-based nanocomplexes as protective nanovehicles for EGCG. Food Hydrocolloids 24(8):735-743.

Su, Ya Lun et al., (2003) Stability of tea theaflavins and catechins. Food Chemistry 83(2):189-195 Epub Jun. 14, 2003.

Zimeri, J. and Tong, C. H. (1999) Degradation Kinetics of (-)-Epigallocatechin Gallate as a Function of pH and Dissolved Oxygen in a Liquid Model System. Journal of Food Science 64(5):753-758.

Zimet, Patricia and Livney, Yoav D. (2009) Beta-lactoglobulin and its nanocomplexes with pectin as vehicles for [omega]-3 polyunsaturated fatty acids. Food Hydrocolloids 23(4):1120-1126 Epub Jun. 28, 2008.

Almajano et al., (2007) Changes in the antioxidant properties of protein solutions in the presence of epigallocatechin gallate. Food Chemistry 101(1): 126-130.

Arts et al., (2002) Interactions between Flavonoids and Proteins: Effect on the Total Antioxidant Capacity. Journal of Agricultural and Food Chemistry 50(5): 1184-1187.

Cabrera et al., (2006) Beneficial effects of green tea—a review. J Am Coll Nutr 25(2): 79-99.

Christiaens et al., (2002) Tryptophan fluorescence study of the interaction of penetratin peptides with model membranes. Eur J Biochem 269(12): 2918-2926.

Chyu et al. (2004) Differential effects of green tea-derived catechin on developing versus established atherosclerosis in apolipoprotein E-null mice. Circulation 109(20): 2448-2453.

de Wit (2009) Thermal behaviour of bovine [beta]-lactoglobulin at temperatures up to 150 ° C. a review. Trends in Food Science & Technology 20(1): 27-34.

Einhorn-Stoll et al., (2005) Formation of milk protein-pectin conjugates with improved emulsifying properties by controlled dry heating. Food Hydrocolloids 19 (2): 329-340.

Fechner et al., (2007) Stability and release properties of double-emulsions stabilised by caseinate—dextran conjugates. Food Hydrocolloids 21 (5-6): 943-952.

Ghosh et al., (2008) Spectrophotometric studies on the interaction between (-)-epigallocatechin gallate and lysozyme. Chemical Physics Letters 452(1-3): 193-197.

Gunasekaran et al., (2007) Use of whey proteins for encapsulation and controlled delivery applications. Journal of Food Engineering 83(1): 31-40.

Hattori et al., (1995) Functional-Changes of Carboxymethyl Potato Starch by Conjugation with Whey Proteins. Journal of Agricultural and Food Chemistry 43 (8): 2007-2011.

Hattori et al., (2000) Functional changes in beta-lactoglobullin by conjugation with cationic saccharides. J Agric Food Chem 48 (6): 2050-2056.

Hiller and Lorenzen (2008) Surface hydrophobicity of physicochemically and enzymatically treated milk proteins in relation to techno-functional properties. Journal of Agricultural and Food Chemistry 56(2): 461-468.

Hiller and Lorenzen (2010) Functional properties of milk proteins as affected by Maillard reaction induced oligomerisation. Food Research International 43 (4): 1155-1166.

Hu et al., (2008) Optimization of fabrication parameters to produce chitosan-tripolyphosphate nanoparticles for delivery of tea catechins. J Agric Food Chem 56(16): 7451-7458.

Kato (2002) Industrial applications of Maillard-type protein-polysaccharide conjugates. Food Science and Technology Research 8 (3): 193-199.

Kim and Lee (2009) Antioxidant activity of Maillard reaction products derived from aqueous glucose/glycine, diglycine, and triglycine model systems as a function of heating time. Food Chemistry 116 (1): 227-232.

Lee et al., (2008) Preparation and characterization of calcium pectinate gel beads entrapping catechin-loaded liposomes. Int J Biol Macromol 42(2): 178-184.

Li et al., (2009) Electrospun Zein Fibers as Carriers to Stabilize (-)-Epigallocatechin Gallate. Journal of Food Science 74(3): C233-C240.

Liu et al., (2007) Antioxidant nature of bovine milk beta-lactoglobulin. Journal of Dairy Science 90(2): 547-555.

Livney (2010) Milk proteins as vehicles for bioactives. Current Opinion in Colloid & Interface Science 15: 73-83.

Livney et al.,(2003) Influence of thermal processing on the properties of dairy colloids. Current Opinion in Colloid & Interface Science 8(4,5): 359-364.

Manderson et al., (1999) Effect of Heat Treatment on Bovine β-Lactoglobulin A, B, and C Explored Using Thiol Availability and Fluorescence. Journal of Agricultural and Food Chemistry 47(9): 3617-3627.

Mori et al., (2010) Covalent binding of tea catechins to protein thiols: the relationship between stability and electrophilic reactivity. Biosci Biotechnol Biochem 74(12): 2451-2456.

Mu et al., (2006) Acidic solution properties of beta-casein-graft-dextran copolymer prepared through Maillard reaction. Journal of Colloid and Interface Science 301 (1): 98-106.

(56) References Cited

OTHER PUBLICATIONS

Neirynck et al., (2007) Influence of pH and biopolymer ratio on whey protein-pectin interactions in aqueous solutions and in O/W emulsions. Colloids and Surfaces A-Physicochemical and Engineering Aspects 298 (1-2): 99-107.

O'Regan and Mulvihill (2010) Sodium caseinate-maltodextrin conjugate hydrolysates: Preparation, characterisation and some functional properties. Food Chemistry 123(1): 21-31.

Pan et al., (2006) Micellization of casein-graft-dextran copolymer prepared through Maillard reaction. Biopolymers 81 (1): 29-38.

Pascal et al., (2009) Study of the interactions between a proline-rich protein and a flavan-3-ol by NMR: Residual structures in the natively unfolded protein provides anchorage points for the ligands. Biopolymers 91(9): 745-756.

Pessen et al., (1985) Proton relaxation rates of water in dilute solutions of [beta]-lactoglobulin. Determination of cross relaxation and correlation with structural changes by the use of two genetic variants of a self-associating globular protein. Biochimica et Biophysica Acta (BBA)—Protein Structure and Molecular Enzymology 828(1): 1-12.

Qi et al., (2009) Improvement of functional properties of acid-precipitated soy protein by the attachment of dextran through Maillard reaction. International Journal of Food Science and Technology 44 (11): 2296-2302.

Riihimaki et al., (2006) Microplate screening assay for binding of ligands to bovine or reindeer [beta]-lactoglobulins. Journal of Biochemical and Biophysical Methods 68(2): 75-85.

Rusli et al., (2006) Stabilization of Oils by Microencapsulation with Heated Protein-Glucose Syrup Mixtures. Journal of the American Oil Chemists' Society 83(11): 965-972.

Serfert et al., (2009) Chemical stabilisation of oils rich in long-chain polyunsaturated fatty acids during homogenisation, microencapsulation and storage. Food Chemistry 113(4): 1106-1112.

Shapira et al., (2010) Beta-casein nanovehicles for oral delivery of chemotherapeutic drugs. Nanomedicine 6(1): 119-26.

Shpigelman et al., (2009) Heat-Induced Beta Lactoglobulin-Based Nanoparticles as Novel Protective Carriers for EGCG in Clear Beverages. Delivery of Functionality in Complex Food Systems, Wageningen, The Netherlands, Oct. 2009—abstract.

Shutava et al., (2009) (-)-Epigallocatechin gallate/gelatin layer-by-layer assembled films and microcapsules. Journal of Colloid and Interface Science 330(2): 276-283.

Siebert et al., (1996) Nature of polyphenol-protein interactions. Journal of Agricultural and Food Chemistry 44(1): 80-85.

Wiese et al., (2009) Protein interactions with cyanidin-3-glucoside and its influence on alpha-amylase activity. Journal of the Science of Food and Agriculture 89(1): 33-40.

Yilmaz and Toledo (2005) Antioxidant activity of water-soluble Maillard reaction products. Food Chemistry 93 (2): 273-278.

Chen, Lingyun et al., (2006) Food protein-based materials as nutraceutical delivery systems. Trends Food Sci Technol 17(5):272-283.

Gosal et al., (2002) Novel Amyloid Fibrillar Networks Derived from a Globular Protein: β-Lactoglobulin. Langmuir 18 (19):7174-7181.

Hong YH and McClements DJ (2007) Formation of hydrogel particles by thermal treatment of beta-lactoglobulin-chitosan complexes. J Agric Food Chem 55(14):5653-5660.

Jameson et al., (2002) Flexibility, functionality and hydrophobicity of bovine β-lactoglobulin. Int Dairy J 12(4):319-329.

Jones OG and McClements DJ (2008) Stability of biopolymer particles formed by heat treatment of beta lactoglobulin/beet pectin electrostatic complexes. Food Biophysics 3(2):191-197.

Ron N. "Beta lactoglobulin as a nano-capsular vehicle for hydrophobic nutraceuticals" [online] 2007 The Technion, Israel Institute of Technology, Haifa, Israel. Retrieved from the internet: URL:http://www.graduate.technion.ac.il/theses/advisors.asp?key=20867> Retrieved on Aug. 6, 2008 abstract.

Ron N. "Beta lactoglobulin as a nano-capsular vehicle for hydrophobic nutraceuticals" Thesis Apr. 1, 2007 pp. 1-45.

Subirade et al., (2003) Whey protein-derived biomaterials and their use as bioencapsulation and delivery systems. Chem Ind 57(12):617-621.

Wang et al., (1997) Binding of Retinoids to (β-Lactoglobulin Isolated by Bioselective Adsorption. J Dairy Sci 80 (6):1047-1053.

Wang et al., (1997) Binding of vitamin D and cholesterol to beta-lactoglobulin. J Dairy Sci 80(6): 1054-1059.

* cited by examiner

DENATURED LACTOGLOBULIN AND POLYPHENOL COASSEMBLIES

FIELD OF THE INVENTION

The present invention is directed to co-assembled nanoparticle composition comprising heat treated β-lactoglobulin and one or more nutraceutical compounds, specifically polyphenols, such as EGCG, compositions comprising same and methods of preparing thereof.

BACKGROUND OF THE INVENTION

Delivery and protection of health-promoting compounds such as polyphenols, including EGCG and related catechins, is an important challenge as polyphenols are not stable in water due to oxidation and are known to be bitter and/or astringent.

A solution to avoid the bitter taste of polyphenols is their encapsulation for preventing contact with the mouth. U.S. Pat. No. 6,190,591 discloses controlled release from discrete, solid particles which contain encapsulated and/or embedded components. JP2005-1245540 discloses a method for masking the astringency and bitterness of polyphenols by inclusion of casein. However, encapsulation is not suitable for any food product. Furthermore, water soluble compounds such as catechin are very difficult to encapsulate since they tend to leak out leading to short shelf life.

US 2010/0159105 discloses a food composition intended to reduce the bitterness of catechin characterized in that it contains at least 100 mg/l of a catechins-$Zn^{++}$ salt precipitate or a polymeric polyphenol compound—$Zn^{++}$ salt precipitate and any mixture thereof.

Nanoparticles offer a suitable vehicle system for protection and delivery of pharmaceutical and nutraceutical agents. U.S. Pat. No. 6,290,974 teaches a composition comprising food additive comprising a preformed complex of β-lactoglobulin and a lipophilic nutrient selected from the group consisting of vitamin A, vitamin D, vitamin E, vitamin $K_1$, cholesterol, and conjugated linoleic acid. In that disclosure the lipophilic nutrient is bound to β-lactoglobulin.

Core-shell nanoparticles of chitosan coated with native and denatured β-lactoglobulin for delivery of nutraceuticals are disclosed in Chen (Chen, et al. (2005) Biomaterials, Vol. 26, pages 6041-6053). Chen teaches that the native β-lactoglobulin has favorable properties compared to the denatured β-lactoglobulin.

WO 2009/130704 by one of the inventors of the present invention discloses a stable colloidal dispersion of nanoparticles comprising complexes of β-lactoglobulin and a polysaccharide, where preferably the stable colloidal dispersion of nanoparticles is transparent in an aqueous medium.

Nowhere in the art has it been taught or suggested to co-assemble nanoparticles of unfolded (denatured) β-lactoglobulin (β-Lg) and polyphenols.

The inventors of the present invention disclosed on Oct. 18, 2009 ($3^{rd}$ International Symposium, 18-21 Oct. 2009, Wageningen, The Netherlands) and in November-December 2010 (Shpigelman, et al. (2010) Food Hydrocolloids, Vol. 24, pages: 735-743) a co-assembled nanoparticle system based on thermally denatured β-lactoglobulin (β-Lg) and polyphenols. Such nanoparticle system has not been disclosed or suggested by the background art.

SUMMARY OF THE INVENTION

The present invention is directed to a co-assembled nanoparticle composition based on a denatured (heat treated, unfolded) globular protein, such as, β-lactoglobulin (β-Lg) and a nutraceutical compound, specifically polyphenols, such as Epigallocatechin-3-gallate (EGCG)—a major catechin found in green tea.

The present invention is based in part on the unexpected discovery that denatured (unfolded) β-Lg binds EGCG more avidly than does native β-Lg. It is further surprising that EGCG degradation rate in the presence of denatured β-Lg is either prevented or becomes significantly slower than in the absence of denatured β-Lg, or in the presence of native β-Lg. In addition, the co-assembled nanoparticle composition of the invention is transparent and having a colloidal stability that meets the requirements for long shelf life. The high colloidal stability of the composition of the invention also renders it suitable for preparing beverages, including, clear beverages. Furthermore, the nanoparticles of the invention are less bitter and less astringent compared to equal concentrations of EGCG alone. The aforementioned properties render the nanoparticle composition of the invention particularly appropriate as an additive to drinks and other food products. Advantageously, the nanoparticle composition of the invention maintains its desired properties, including, particle size and colloidal stability, even after reconstitution from a dried (e.g. freeze-dried) state, which makes it highly suitable for commercial use. Moreover, during gastric digestion very little release of the EGCG from the nanoparticles is observed, thus establishing that the nano-particle composition of the invention provide an efficient vehicle for the delivery of EGCG and other polyphenols to the small intestine.

The aforementioned advantages among others attribute to the utility of the composition, specifically, as a stable composition of polyphenols for the production of clear soft drinks enriched with polyphenols, such as EGCG.

According to a first aspect, the present invention provides a nanoparticle composition comprising a plurality of nanoparticles, each nanoparticle comprising denatured β-lactoglobulin and at least one nutraceutical compound. According to one embodiment, the composition is devoid of polysaccharides or the content of polysaccharides is negligible, such as, less than 0.1%. In some embodiment where polysaccharides are present, then they are not attracted to the protein (e.g. uncharged polysaccharides, or carrying the same sign of charge as the protein).

According to another embodiment, the denatured β-lactoglobulin is obtained by at least one route selected from the group consisting of: heat, pressure, pH, and chemical reagents (e.g. solvents).

According to another embodiment, the plurality of nanoparticles exhibits a particle size distribution within the range of 1 nm to 500 nm. According to yet another embodiment, the plurality of nanoparticles exhibits a particle size distribution within the range of 1 nm to 50 nm.

According to yet another embodiment, the plurality of nanoparticles exhibit a volume weighted average particle size lower than 100 nm. According to yet another embodiment, the plurality of nanoparticles exhibit a volume weighted average particle size lower than 80 nm. According to yet another embodiment, the plurality of nanoparticles exhibit a volume weighted average particle size lower than 50 nm.

According to yet another embodiment, the at least one nutraceutical compound is a polyphenol. According to yet another embodiment, the at least one nutraceutical compound is catechin. According to yet another embodiment, the at least one nutraceutical compound is a catechin selected from EGCG, epicatechin gallate (ECG), epigallocatechin (EGC) and epicatechin (EC).

According to yet another embodiment, the pH of the nanoparticle composition is within the range of 6.0 to 7.5 According to yet another embodiment, the molar ratio β-lactoglobulin:nutraceutical compound is in the range of 1:1 to 1:20.

According to yet another embodiment, the nanoparticle composition comprises a plurality of nanoparticles, each nanoparticle is consisting of denatured β-lactoglobulin and at least one nutraceutical compound, such as, EGCG.

According to another aspect, the present invention provides a nutritionally-fortified liquid composition comprising: aqueous solution and the nanoparticle composition of the invention. According to one embodiment, the nutritionally-fortified liquid composition has turbidity within the range of 0 to 0.4, preferably 0 to 0.1 (absorbance at 600 nm). According to another embodiment, the nutritionally-fortified liquid composition further comprising at least one agent selected from the group consisting of: vitamins, minerals, aminoacids, antioxidants, enzymes, hormones, botanicals, herbals, dietary supplements, pro-biotics, pre-biotics, soluble fibers and energy sources. According to yet another embodiment, the nutritionally fortified liquid further comprises additional components including, but not limited to, aromas, flavors, and colors.

According to yet another aspect, the present invention provides a pharmaceutical composition comprising the nanoparticle composition of the invention and a pharmaceutically acceptable carrier.

According to one embodiment, the pharmaceutical composition further comprises at least one pharmaceutical agent. According to another embodiment, the pharmaceutically acceptable carrier is an excipient mixed with the nanoparticle composition. According to an alternative embodiment, the nanoparticle composition is enclosed within the pharmaceutically acceptable carrier. According to some embodiments, the at least one nutraceutical compound is EGCG.

The present invention further provides a method of treating or preventing a disease associated with lack of said at least one nutraceutical compound, comprising administering to a person in need thereof said pharmaceutical composition, wherein the disease is selected from the group consisting of: cardiovascular disease, neurodegenerative disease, obesity and cancer. According to yet another embodiment, the pharmaceutical composition is administered orally by any means known in the art.

The present invention further provides a method of preparing a nanoparticle composition comprising denatured β-lactoglobulin and at least one nutraceutical compound, comprising:

(a) providing a solution comprising β-lactoglobulin;
(b) providing a solution comprising at least one nutraceutical compound;
(c) incubating the β-lactoglobulin solution at a temperature within the range of 65° C. to 99° C. for 0.5 to 45 minutes, thereby obtaining denatured β-lactoglobulin; and
(d) mixing the solution comprising the at least one nutraceutical compound into the β-lactoglobulin solution thereby obtaining a nanoparticle composition comprising a plurality of nanoparticles comprising denatured β-lactoglobulin and the at least one nutraceutical compound.

According to one embodiment, the β-lactoglobulin solution is cooled down to room temperature prior to step (c).

According to another embodiment, the at least one nutraceutical compound is selected from the group consisting of a polyphenol, catechin, EGCG, ECG, EGC and EC. According to yet another embodiment, the at least one nutraceutical compound is a polyphenol and the pH of the solution at step (b) is within the range of pH where the at polyphenol is stable, e.g. within the range of 2 to 3 pH units. According to yet another embodiment, the pH of the nanoparticle composition is within the range of 6.0 to 7.5.

According to yet another embodiment, the molar ratio β-lactoglobulin to the at least one nutraceutical compound in the nanoparticle composition is within the range of 1:1 to 1:20.

According to yet another embodiment, the plurality of nanoparticles exhibit particle size distribution within the range of 1 nm to 500 nm, 1 nm to 200 nm, 1 nm to 100 nm or 1 nm to 50 nm.

According to yet another embodiment, the plurality of nanoparticles exhibit a volume weighted average particle size lower than 100 nm. According to yet another embodiment, the plurality of nanoparticles exhibit a volume weighted average particle size lower than 80 nm. According to yet another embodiment, the plurality of nanoparticles exhibit a volume weighted average particle size lower than 50 nm.

According to yet another embodiment, the nanoparticle composition comprises heat treated β-lactoglobulin and EGCG, wherein the particle size distribution of said nanoparticles is within the range of 1 nm to 50 nm and the pH is within the range of 6.0 to 7.5.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The invention is directed to a co-assembled nanoparticle composition based on a protein such as β-lactoglobulin (β-Lg) and one or more nutraceutical compounds, specifically polyphenols, such as EGCG, wherein the composition is devoid of polysaccharides.

The terms "co-assembled nanoparticle composition", "nanoparticle system", "nanoparticles", "nanocomplexes" and "coassemblies" among others, as used herein, refer to particles, including but not limited to, spherical nanoparticles, that are nano-sized particles having a volume-weighted average diameter ranging from about 1 nm to about 500 nm, more typically from about 1 nm to about 50 nm, as determined by methods known in the art, such a, static and dynamic light scattering, and transmission electron microscopy. More specifically, these terms refer to particles comprising denatured β-lactoglobulin and one or more nutrients, such as polyphenols. This term also refers to particles comprising denatured β-lactoglobulin and one or more nutrients, such as polyphenols and devoid of polysaccharides.

The term "nutraceutical" refers to any bioactive compound that is a food or a food component which provides health and medical benefits, including the prevention and treatment of disease. Nutraceuticals include isolated nutrients, dietary supplements and components of specific diets, herbal products and beverages. In particular embodiments, this term refers to polyphenols.

According to some embodiments, the one or more nutraceutical compounds is a polyphenol. According to other embodiments, the nutraceutical compound is catechin. According to further embodiments, the nutraceutical compound is a catechin selected from EGCG, epicatechin gallate (ECG), epigallocatechin (EGC) and epicatechin (EC).

Figure 1:
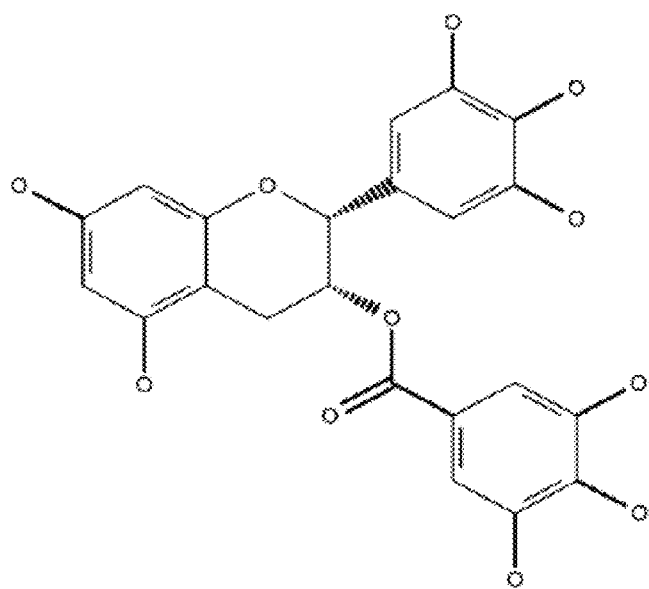
FIG. 1 represents chemical structure of (−)-Epigallocatechin-3-gallate (EGCG) (SciFinder 2009, CAS registry number 989-51-5; In: Chemical abstracts service).

Delivery and protection of sensitive water-soluble health-promoting compounds is an important challenge. EGCG and related catechins occur naturally in several types of plants, including tea, and thus have a long history of safety as a component of a food item. EGCG (FIG. 1) is the major catechin found in green tea, comprising 50%-60% of the total catechin mass.

The potential health benefits associated with tea consumption have been partially attributed to the antioxidative and free-radical quenching properties of tea polyphenols. Tea and especially green tea preparations have been shown to trap reactive oxygen species, such as superoxide radical, singlet oxygen, hydroxyl radical and others. EGCG was found to be the most effective tea polyphenol in quenching the majority of reactive oxygen species. Animal studies indicated that the consumption of green tea and green tea products with high levels of EGCG and other catechins may have a significant effect toward the prevention of tumors, cardiovascular disease, neurodegenerative disease, obesity and other adverse medical conditions. In recent years the possible cancer preventive activity of EGCG received much attention and was demonstrated in animal models and on many different organs. Inhibitory activity was demonstrated during initiation and progression stages of carcinogenesis. Despite the current lack of definite knowledge of the specific cancer prevention mechanisms of EGCG and green tea, numerous animal studies and some human epidemiological studies have shown positive results. A recent large cohort study Suzuki, et al. (2009, Annals of Epidemiology, Vol. 19, pages 732-739) observed for persons drinking seven or more cups of green tea per day a significant reduction in morbidity and mortality due to cardiovascular disease and in general mortality, showing that probably large amounts of green tea polyphenols are necessary for the protective effect.

Green tea catechins are very unstable in neutral and alkaline solutions but are relatively stable under acidic conditions. It was found that EGCG degraded faster with the increase of pH, oxygen concentration or temperature. EGCG was found to be unstable in sodium phosphate buffer (pH 7.4), at which conditions 80% of the EGCG was lost in only 3 hr. It was also shown that green tea catechins degraded by at least 50% during the first month of storage in commercial soft drinks, including acidic ones. EGCG which forms a colorless aqueous solution when freshly dissolved, degrades irreversibly to a yellowish-brown solution of the deterioration products, mainly through oxidation and dimer formation. This color change to brown is clearly undesired for the beverages industry. In addition, the lack of stability presents significant challenges to the design of a vehicle that will allow EGCG enrichment in a diet, and especially in clear beverages, while providing the necessary protection to this sensitive water-soluble molecule.

Beta-lactoglobulin (β-Lg, 18.4 kDa, 162 amino acids) is the major whey protein in cow milk and accounts for about 10% of the total milk proteins, i.e. approximately 50-55% of the total whey proteins.

β-Lactoglobulin has 2 disulfide bonds (Cys106-Cys119 and Cys66-Cys160), and a free thiol at Cys121. At room temperature and at neutral to slightly acidic pH the protein is mostly present at a native dimeric state while at pH values of 3.7-5.1 β-Lg was found to partly exist as octamers. Heating induces aggregation of β-Lg by a chain-reaction of sulfhydryl-disulfide interchange (Livney et al., Journal of Agricultural and Food Chemistry, 51:8098-8106, 2003). Whey proteins can form nanoparticles thereby offer the possibility of entrapping bioactive compounds, without covalently bonding them. Recently, some of the inventors of the present invention have demonstrated that native β-Lg can be used (preferably in combination with pectin) as a nanovehicle for delivery of hydrophobic nutraceuticals such as ω-3 polyunsaturated fatty acids (Zimet & Livney, 2009, Food Hydrocolloids, 23:1120-1126). Native β-Lg was also suggested as a carrier to improve the aqueous solubility and photostability of resveratrol (a polyphenol from grapes). It was also shown that β-Lg is a mild temperature-dependent antioxidant and the free thiol group is likely to be involved in this antioxidant activity. A weak binding of EGCG to native bovine and reindeer β-Lg has been reported and it is known that EGCG binds to a wide variety of proteins, apparently by a combination of hydrophobic interactions and hydrogen bonds.

The present invention provides a co-assembled nanoparticle composition comprising a denatured (unfolded) protein, such as, heat treated β-Lg, and at least one nutraceutical compound, specifically polyphenols, such as EGCG, and, optionally, without polysaccharides. According to certain embodiments, the co-assembled nanoparticle composition is consisting of β-lactoglobulin (β-Lg) and EGCG.

It is to be understood that 'thermally treated' or 'heat treated' β-lactoglobulin according to the present invention is β-lactoglobulin incubated in a temperature within the range of 65° C. to 99° C., 70° C. to 90° C., or 75° C. to 85° C. The incubation time ranges from 0.5 to 45 min., 0.5 to 30 min., 0.5 to 25 min. In some embodiment, the incubation time is about 20 minutes at a temperature of about 75° C. to 85° C. According to other embodiments, the denatured β-lactoglobulin is heat treated β-lactoglobulin.

The terms "denatured β-lactoglobulin", "heat treated β-lactoglobulin" and "unfolded β-lactoglobulin" refer to β-lactoglobulin that lost its secondary or tertiary structure. In one embodiment, the loss of secondary or tertiary structure is complete. In an alternative embodiment, the loss of secondary or tertiary structure is partial. In another embodiment, the change in secondary structure may be of at least 1%, more typically at least 5%, in the intensity of the 222 nm peak as measured by circular dichroism, compared to the native protein.

The nanoparticles of the invention comprise discrete particles having a volume-weighted average particle size above 1 nm but smaller than 1,000 nm, often smaller than 500, 400 nm, 200 nm, 100 nm or even 50 nm.

The term "particle size" as used herein particularly refers to the size of colloidal particles. Typically, the particle size is evaluated for a spherical object and thus is defined by its diameter. However, the shape of typical particles is likely to be irregular and non-spherical. Thus, the quantitative definition of particle size must be adjusted such that it also applies to non-spherical particles. The common definitions for particle size are based on replacing a given particle with an imaginary sphere having one of the properties identical with the particle. These properties include: volume, weight, area or a drag coefficient (a dimensionless number characterizing the overall drag of an object).

For particles with sizes below a micrometer the definition is more complex since for small particle thickness of interface layer becomes comparable with the particle size. As a result, position of the particle surface becomes uncertain. The average particle size for an ensemble (collection) of particles presents another problem. In real systems the particles are usually ensembles having different sizes and there is often a need to define a certain average or median particle size for the ensemble of particles. The average particle size includes, but is not limited to, arithmetic, geometric and logarithmic average, and may correspond to a number-weighted average, a mass-weighted average, a volume-weighted average, a viscosity-weighted average, a Z-weighted average among other types of average known in the art. In a particular embodiment, the average particle size of the nanoparticles of the invention is a volume-weighted average.

Several methods for measuring particle size are known in the art. The methods are based on light, x-rays, ultrasound, electric field, gravity, or centrifugation.

The terms "particle size distribution" and "PSD" are interchangeably used herein and refer to values or a mathematical function that define the relative amounts of particles present, sorted according to size in a powder, granular material, or particles dispersed in fluid.

It is important to note that PSD is usually defined by the method by which it is determined which is only applied on a representative sample. PSD may be expressed as a "range" analysis, in which the amount in each size range is listed in order or in "cumulative" form, in which the total of all sizes "retained" or "passed" by a single parameter is given for a range of sizes. Range analysis is suitable when a particular ideal mid-range particle size is required and cumulative analysis is used where the amount of "under-size" or "over-size" must be controlled. Thus, the term "size" is open to a wide range of interpretations.

Measurement techniques include sieve analysis, air elutriation analysis, photoanalysis, electroresistance counting methods, sedimentation techniques, laser diffraction methods, acoustic spectroscopy or ultrasound attenuation spectroscopy and optical counting methods among others.

In sieve analysis the powder is separated on sieves of different sizes and the PSD is defined in terms of discrete size ranges based on the sizes of the sieves that are used. The PSD is usually determined over a list of size ranges that covers nearly all the sizes present in the sample. Some methods of determination allow much narrower size ranges to be defined than can be obtained by use of sieves, and are applicable to particle sizes outside the range available in sieves. This method is simple, cost effective, and easily interpreted. However, many PSDs are concerned with particles too small for separation by sieving to be practical since the very fine sieves are fragile. In addition, the amount of energy used to sieve the sample is arbitrarily determined where over-energetic sieving causes attrition of the particles and thus changes the PSD, while insufficient energy fails to break down loose agglomerates.

Methods that are dominant in industrial PSD determination are the laser diffraction methods which depend on analysis of the "halo" of diffracted light produced when a laser beam passes through a dispersion of particles in air or in a liquid. The angle of diffraction increases as particle size decreases, so that this method is particularly good for measuring sizes between 0.1 and 3,000 μm. Advanced sophisticated data processing and automation allows this to be a suitable industrial method.

The nanoparticle composition of the invention preferably have a content of more than 0.1% w/w of β-Lg but less than 2% w/w of β-Lg. In addition, the ratio of β-Lg:polyphenol in the nanoparticles of the invention is between 1:1 to 1:20 or 1:2 to 1:10.

Furthermore, the pH of the nanoparticle composition of the invention is the pH suitable for use in beverages such as mineral water, green tea beverages, milk beverages and more. The pH may range between 6.0 to 7.5 pH units. In some embodiments the pH is about 6.5 to 7.0. In other embodiments, the pH is about 6.6 to 6.9. Other alternatives are listed in Table 3.

The present invention further provides a method of manufacturing the nanoparticle composition of the invention, the method comprising:
 (a) providing a protein solution comprising β-Lg;
 (b) providing a nutraceutical solution comprising at least one nutraceutical compound, preferably a polyphenol;
 (c) incubating the protein solution at a temperature within the range of 65° C. to 99° C. thereby obtaining a protein solution comprising denatured β-Lg; and
 (d) mixing the nutraceutical solution with the protein solution of step (c), thereby obtaining a nanoparticle composition comprising said at least one nutraceutical compound and denatured β-Lg.

According to one embodiment, step (d) is carried on by stirring. According to another embodiment, step (d) method further comprises cooling the nanoparticle composition to room temperature.

According to yet another embodiment, the pH of the nutraceutical solution is low in order to protect the stability of the at least one nutrient. According to yet another embodiment, the nutraceutical solution comprises a polyphenol which is soluble in acidic pH. According to yet another embodiment, the nutraceutical solution comprises a polyphenol which is stable in acidic pH. According to yet another embodiment, the nutraceutical solution comprises EGCG, wherein the pH of the nutraceutical solution is within the range of 2 to 3 pH units. According to yet another embodiment, the nutraceutical solution comprises a polyphenol which is stable in acidic pH such that the acidic nutraceutical solution is added onto the neutral protein solution, dropwise, in order to avoid degradation of the polyphenol. As said polyphenol (e.g. EGCG) is unstable at neutral or basic pH it is material to mix the acidic polyphenol solution with the neutral protein solution without affecting the stability of the polyphenol. Protecting the polyphenol from degradation may be achieved by adding a small volume of the acidic polyphenol solution into the large volume of the protein solution.

According to yet another embodiment, the protein solution of step (c) is heated at 75° C. or 85° C. for 0.5 to 45 min., or for about 20 min. Advantageously, the composition comprises only two essential components, the β-Lg protein and the nutraceutical compound, thereby the manufacturing process is relatively straightforward and cost effective, as compared to nanoparticle composition comprising three or more essential components, such as, nanoparticle compositions that require the presence of a polysaccharide in addition to the protein and the nutraceutical compound.

The term "room temperature" as used herein refers to this term as commonly used in the art. For example, room temperature is often indicated by general human comfort, with the common range of 20° C. (68° F.) to 28° C. (82° F.).

The present invention further provides a new, shelf-stable, ready-to-drink nutritional functional product, comprising water and the nanoparticle composition of the invention. The nutritional product of the invention may further comprise other dietary supplements, and/or one or more additives. The nutritional product of the invention is suitable for consumption by humans, and also for animals.

In one embodiment, the nutritional functional product is in a liquid form which may incorporate suitably flavored syrups, aqueous suspensions, and flavored emulsions with edible oils such as cottonseed oil, sesame oil, coconut oil, or peanut oil, as well as elixirs and similar pharmaceutical vehicles.

Advantageously, the nanoparticle composition of the invention is colorless, as determined visually and by spectroscopic measurements. Moreover, the nanoparticle composition of the invention is transparent and the turbidity of a solution consisting of the nanoparticle composition and a liquid carrier (e.g. water) is within the range of 0 to 0.05, 0 to 0.1, or 0 to 0.4 measured as spectrophotometric absorbance at 600 nm. Typically, the turbidity of the solution is below 0.4, below 0.1, or below 0.05.

In addition to clarity, the nanoparticle composition of the invention includes the following advantages:
 (i) Strong binding of the EGCG to preheated β-Lg, stronger than binding of EGCG to native β-Lg;
 (ii) Only two essential components, namely, denatured β-Lg and a nutraceutical compound;
 (iii) Lower to negligible EGCG degradation rate compared to that of EGCG in the absence of denatured β-Lg;
 (iv) Transparency with high colloidal stability over time;
 (v) Lower to insignificant bitterness and astringency compared to equal concentrations of EGCG alone;
 (vi) Small particle size within the range of 1-500 nm, preferably 1-100 nm or 1-50 nm;
 (vii) Maintaining all properties, including, particle size and colloidal stability, after reconstitution from a freeze-dried state; and
 (viii) Minor release of EGCG from the nanoparticles during gastric digestion.

The aforementioned advantages among others attribute the composition of the invention to therapeutic and nutritional utilities, such as, an efficient vehicle for the delivery of polyphenols to the small intestine and a stable composition for the production of clear soft drinks enriched with polyphenols, such as EGCG.

For the nutritional functional product to be palatable, sweeteners, such as, sugar, and/or sugar substitutes, and also organic and/or inorganic acids, and/or flavorants may be added.

Viscosifying agents may be added to the drink, preferably, without adding significant taste and/or calories.

In some embodiments, unnecessary additives chemicals and sweeteners are avoided whenever possible. Clearly, the preferred water used for the nutritional functional product of the invention is safe and particularly suitable for the preparation of beverages.

The present invention further provides a pharmaceutical composition comprising as the active ingredient the protein-polyphenol co-assemblies of the invention.

In making the compositions of the present invention, the nanoparticle composition of the invention is usually mixed with an excipient, diluted by an excipient or enclosed within such a carrier which can be in the form of a tablet, capsule, sachet, paper, solution in a vial or other containers. Some examples of suitable excipients include lactose, dextrose, sucrose, sorbitol, mannitol, calcium phosphate, alginates, tragacanth, gelatin, calcium silicate, microcrystalline cellulose, polyvinylpyrrolidone, cellulose, water, syrup, and methyl cellulose. In alternative embodiment, the nanoparticle composition of the invention may be mixed with starches and gum acacia. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the present invention can be formulated so as to provide quick, sustained or delayed release of the active ingredient after administration to the patient or consumer by employing formulations and procedures known in the art.

For preparing solid compositions such as tablets the nanoparticle composition of the invention is mixed with a pharmaceutical excipient to form a solid formulation composition containing a homogeneous mixture. When referring to these formulations as homogeneous, it is meant that the nanoparticle composition of the invention is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In another embodiment, the pharmaceutical composition of the invention comes in the form of kits or packages containing at least one dosage form comprising as the active ingredient the nanoparticle composition of the invention, for example, a nanoparticle composition consisting of EGCG and β-Lg. Illustratively, the kits or packages contain at least one dosage form comprising the active ingredient in amounts sufficient for the proper dosing. In another embodiment, the kits contain at least one dosage form for oral administration, for example, a tablet or capsule. The pharmaceutical composition of the invention can be packaged in the form of kits or packages in which the daily (or other periodic) dosages are arranged for proper sequential or simultaneous administration. The present invention further provides a kit or package containing a plurality of dosage units, adapted for successive daily administration, each dosage unit comprising the nanoparticle composition of the present invention. In one embodiment, the composition contains a plurality of dosages to be taken daily, or weekly, or monthly, via oral administration (as commonly practiced in the oral contraceptive art).

The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The present invention further provides a method of treating or preventing a disease associated with lack of said nutraceutical compound, comprising administering to a person in need thereof the pharmaceutical composition of the invention, wherein the disease is selected from the group consisting of: cardiovascular disease, neurodegenerative disease, obesity and cancer.

The present invention further provides the use of a nanoparticle composition comprising a plurality of nanoparticles, each nanoparticle comprises a denatured globular protein and a nutraceutical compound for the manufacture of a medicament for treating or preventing a disease associated with lack of said nutraceutical compound selected from the group consisting of: cardiovascular disease, neurodegenerative disease, obesity and cancer.

The globular protein may be selected from the group consisting of globulins and albumins. The globular protein may be β-lactoglobulin. The plurality of nanoparticles may exhibit a particle size distribution within the range of 1 nm to 1,000 nm, 1 nm to 500 nm, and even 1 to 50. The nutraceutical may be a polyphenol, or catechin, such as, EGCG, EGC, EC and ECG.

These and further embodiments will be apparent from the detailed description and examples that follow.

EXAMPLES

Example 1

Entrapment of EGCG by Co-Assembly with Preheated β-Lg

To protect EGCG against oxidative deterioration, a new method of nanoentrapment of EGCG within co-assembled β-Lg-EGCG nanoparticles was developed.

Without wishing to be bound by any theory or mechanism, it was hypothesized that denatured β-Lg would serve as a good protector, both because it is a mild antioxidant and because EGCG has good affinity to proteins, particularly proteins with open structures, like saliva, gelatin and casein. Thus, unfolding of β-Lg would improve its binding affinity to EGCG. Moreover, β-Lg can form nanoaggregates upon heating at low ionic strength and pH not close to the pI (5.35), due to intermolecular electrostatic repulsion, which prevents extensive aggregation and gelation.

Beta-lg solution was prepared in a buffer solution (30 mM phosphate buffered solution; PBS, target pH=7) containing 0.02% sodium azide (as preservative for experimental use only) made by dissolving 0.234 gr $NaH_2PO_4.2H_2O$, 0.267 gr $Na_2HPO_4.2H_2O$ and 0.02 gr sodium azide ($NaN_3$) in 100 ml HPLC grade water. The buffer was used without further pH correction. Beta-Lg was dissolved in pH 7 buffer and stirred overnight at room temperature. The exact final pH of the solution is noted for each of the experiments. The addition of β-Lg or EGCG did not appreciably modify the pH. Fresh EGCG solutions were prepared daily using a 30 mM PBS for a target pH=2.5 that contained 0.102 ml $H_3PO_4$ (85%) with 0.234 gr $NaH_2PO_4.2H_2O$ diluted by 100 ml HPLC grade water (the exact final pH of the solution is noted for each of the experiments. The buffers were used without further pH correction). For the preparation of a 5 mM buffer for the dynamic light scattering experiment, 0.017 ml H$_3$PO$_4$ (85%) and 0.039 gr NaH$_2$PO$_4$.2H$_2$O were diluted with 100 ml HPLC grade water.

Different amounts of EGCG were added to commercial mineral water (Aqua Nova™, pH 6.9), to obtain concentrations in the range 0.01%-0.5%. Aliquots of 2.5 ml EGCG solution were transferred to 1 cm path length spectrophotometer cuvettes and covered with parafilm to prevent evaporation. The absorbance at 425 nm was observed for 268 hours using an Ultrospec 3000 spectrophotometer (GE Healthcare, Waukesha, Wis., USA). A similar experiment was performed in 30 mM PBS, pH=6.8.

For preparation β-Lg-EGCG nanoparticles EGCG solution (in PBS, pH~2.5) at room temperature was added to β-Lg (in 30 mM PBS pH~6.9) which was heated at 75° C. or 85° C. in a water bath for 20 minutes. After addition of EGCG to the protein solution the samples were vortexed for 20 seconds and allowed to cool down to room temperature (21-25° C.). In both cases the solution reached 40° C. in about 4.5 min and 30° C. after 11 min.

Example 2

Binding of EGCG to Native and to Heat Denatured β-Lg

The binding and co-assembly of EGCG and β-Lg at different conditions, thermal treatments, concentrations and ratios, was studied. Optimal results were obtained following a 75° C., 20 min heat treatment of the protein solution (pH~6.9, in a low ionic strength buffer), followed by addition of acid-buffered EGCG (pH~2.5), vortexing for 20 sec, and allowing the composition to cool to room temperature.

Intrinsic protein fluorescence can be used to study binding properties and structural transitions of proteins. This technique was applied to study the binding of various molecules to β-Lg and was also used to study EGCG interaction with different proteins. Fluorescence spectroscopy was applied herein to compare the binding affinities of EGCG to native β-LG, and after preheating the protein to 75° C. or 85° C. for 20 minutes. It is based on exciting at 280 nm the Trp and Tyr residues of bovine β-Lg (bovine β-Lg contains two Trp residues and four Tyr residues) and at 295 nm where only Trp residues are excited though the quantum yield of the Trp itself is smaller than that at 280 nm.

All fluorescence measurements were performed at room temperature. β-Lg solution (2.09 μM in 1.9 ml of 30 mM PBS, pH 6.86) was heated at 75° C. for 20 minutes, or kept at room temperature. The co-assembly preparation process was done as described above. All measurements were performed after equilibrating the solutions at room temperature for 3 hours. EGCG solutions were 0-400 μM in 0.1 ml of 30 mM PBS, pH 2.44. All samples were prepared in triplicates. The pH of the final solutions was 6.86. β-Lg fluorescence was measured at constant protein concentration of 2 μM and EGCG concentrations of 0-20 μM using a Fluorolog 3-22 spectrofluorometer (Horiba, Jobin Yvon, Longjumeau, France) at a Right-Angle mode. Emission spectra were recorded from 290 to 510 nm with an excitation wavelength of 280 nm, and from 305 to 520 nm with an excitation wavelength of 295 nm, employing 5 nm slit widths. The statistical analysis and non-linear curve fitting were performed using Origin 8 (OriginLab, Northampton, USA).

Figure 3A:
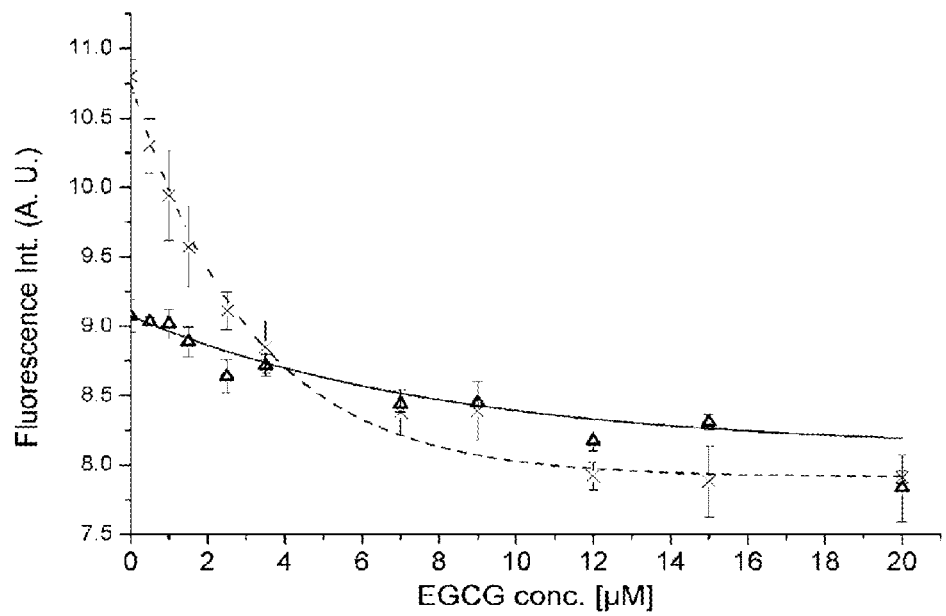
FIG. 3A exhibits fluorescence intensity of 2 μM β-Lg at 23° C. (excitation: 280 nm, emission: 343 nm) with rising EGCG concentrations for the preheated protein (75° C. for 20 minutes; x) and for the native protein (triangle). Error bars represent standard error.
Figure 3B:
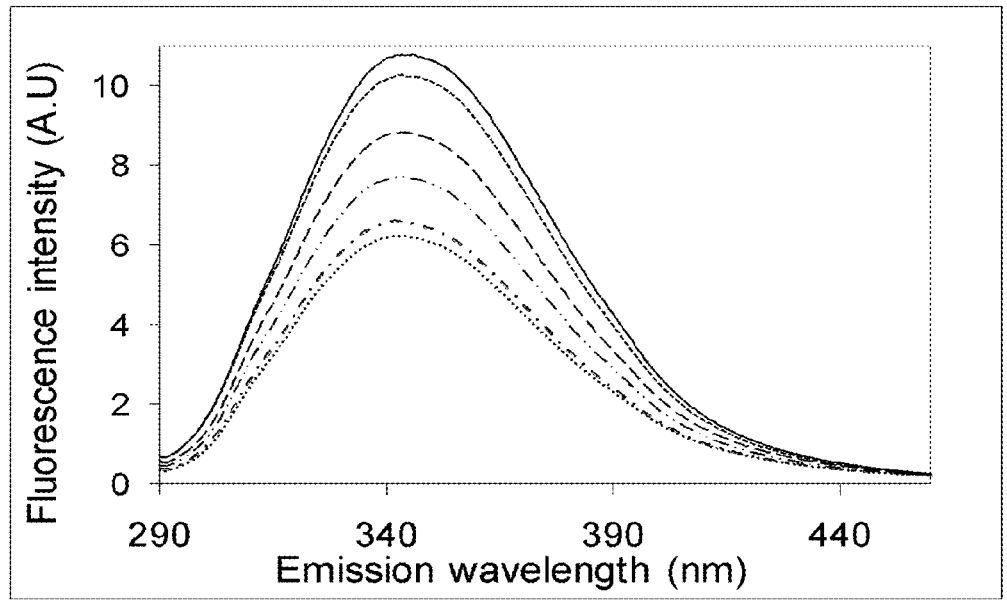
FIG. 3B shows fluorescence spectra of 2 μM β-Lg in PBS pH 6.87 following excitation at 280 nm at 23° C. with rising EGCG concentrations (0, 0.5, 2.5, 7, 15, 20 μM) after preheating of the protein at 75° C. for 20 minutes.

In a preceding 3D excitation/emission spectra-scan it was found that excitation at 280 nm effected maximal emission of the protein. As can be seen in FIG. 3B increasing concentrations of EGCG resulted in increased quenching of β-LG fluorescence between ~290 and ~440 nm. Trp61 is reportedly quenched in the native state due to proximity to the Cys66-Cys160 disulfide bond, while Trp 19 is located in a non-polar environment within the cavity of the β-barrel structure, and is responsible for most of the Trp (and the protein) fluorescence. A small shift in the maximal emission wavelength of the protein occurred upon heating and was more clearly observed at the excitation wavelength attributed to Trp alone (295 nm). As only small shifts in the maximal wavelength occurred, all analyses were performed at emission of 343 nm for both excitation wavelengths. When studying the binding of EGCG to β-LG by fluorescence, it is important to keep in mind that EGCG, and not only β-LG, absorbs energy, both at the protein's excitation and, to a lower extent, at the emission wavelengths. Consequently, an inner filtering effect occurs, which intensifies with increasing EGCG concentration, reducing the amount of available energy to excite the protein's fluorescent groups and absorbing some of the emitted energy too. To overcome this effect, the emission at 343 nm was corrected according to Beer-Lambert's law, using equation 1:

$$F = F_u \cdot 10^{QL(\epsilon\lambda_{ex} + \epsilon\lambda_{em})}$$ (Equation 1)

where Fu is the measured, uncorrected emission intensity, ϵλex and ϵλem—the molar extinction coefficients of EGCG at the excitation and emission wavelengths respectively (measured spectrophotometrically, in the same buffer), Q is the quencher (EGCG) concentration in the cell and L is the path length assumed to be 0.5 cm each for the excitation and emission.

EGCG itself was found not to fluoresce at the emission wavelengths of the protein. The corrected protein emission at 343 nm (excitation at 280 nm), with and without preheating of the protein, is presented in FIG. 3A as a function of EGCG concentration. The difference in fluorescence is apparent, especially at low EGCG concentrations, and the extent of quenching is significantly larger for the preheated protein.

Figure 4A:
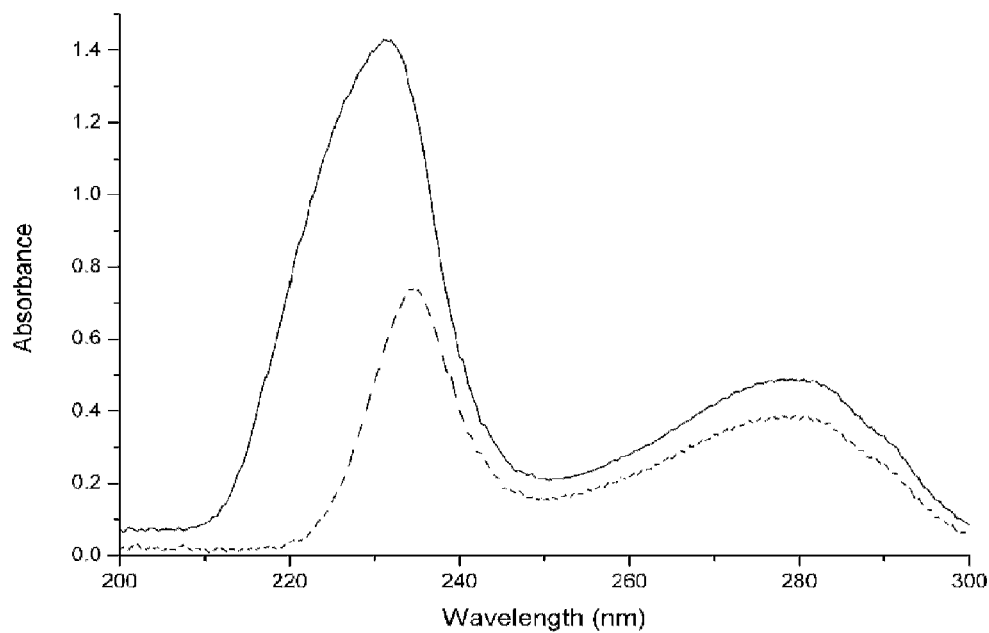
FIG. 4A shows the UV absorbance spectrum over the range of 200-330 nm of preheated β-Lg alone (solid line), and the absorbance spectra difference between UV absorbance spectrum of preheated β-Lg-EGCG and UV absorbance spectrum of EGCG alone (dashed).
Figure 4B:
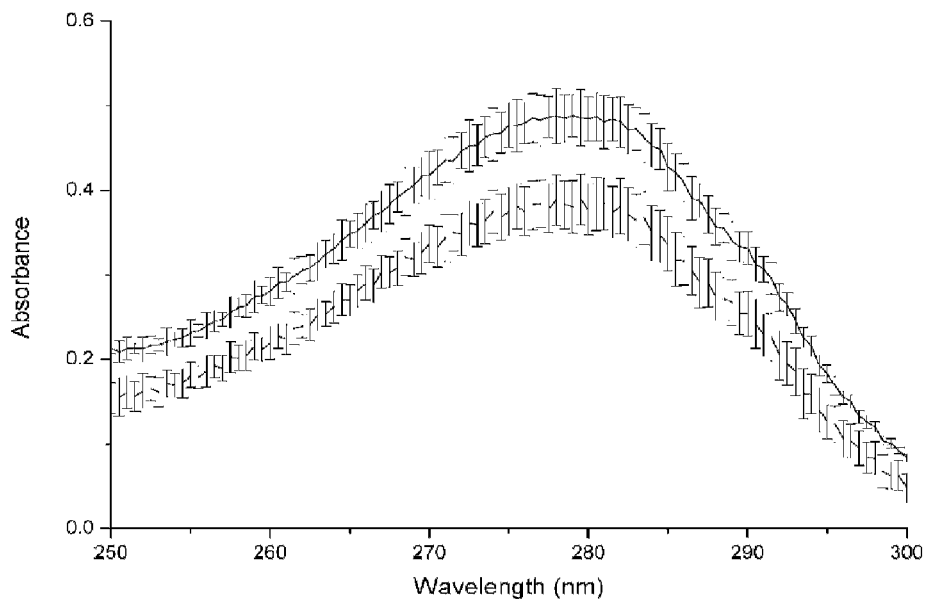
FIG. 4B shows the UV absorbance spectrum over the range of 250-300 nm of preheated β-Lg alone (solid line), and the absorbance spectra difference between UV absorbance spectrum of preheated β-Lg-EGCG and UV absorbance spectrum of EGCG alone (dashed; Error bars represent standard error).

The use of fluorescence to study binding requires attention to the possibility of non binding-induced (dynamic) quenching. One of the methods for distinguishing dynamic quenching from static (binding) quenching is by examining the absorbance spectra of the fluorophore. Whereas dynamic quenching affects only the excited state of the fluorophore, static quenching, frequently results in the perturbation of the absorbance spectrum of the fluorophore, due to formation of ground state (bound) complexes. Accordingly, absorbance spectroscopy was applied to confirm the existence of a static quenching mechanism. EGCG-β-Lg co-assemblies were prepared as described above, using 1% EGCG solution (21.82 mM in 0.05 ml, 30 mM PBS, pH 2.44) and 1% β-Lg (0.54 mM in 0.95 ml 30 mM PBS pH 6.86), heated (75° C., 20 min), or kept at room temperature. Appropriate controls of β-Lg without EGCG and of EGCG without β-Lg at the respective concentrations and pH values were performed. To obtain concentrations that are in the linear absorbance range of the spectrophotometer the solutions were further diluted by PBS pH 6.86. The final EGCG concentration was 54.55 μM (0.0025%), the final β-Lg concentration was 25.82 μM (0.0475%), the molar ratio was ~2:1 (EGCG:β-Lg), and the pH of the final solutions was 6.86. Similar ground state complexes were reported for EGCG-lysozyme interaction and for the interaction of β-Lg with resveratrol. The UV absorbance spectrum of β-Lg and the difference between the spectrum of preheated β-Lg with EGCG and that of EGCG alone at the same concentration are shown in FIGS. 4A (200-330 nm) and 4B (250-300 nm).

Evidently, the difference cannot be superposed within the experimental error, supporting the important role of binding-induced quenching mechanism in this case. Similarly, existence of static quenching was confirmed for EGCG-native-β-Lg complexes.

Figure 5:
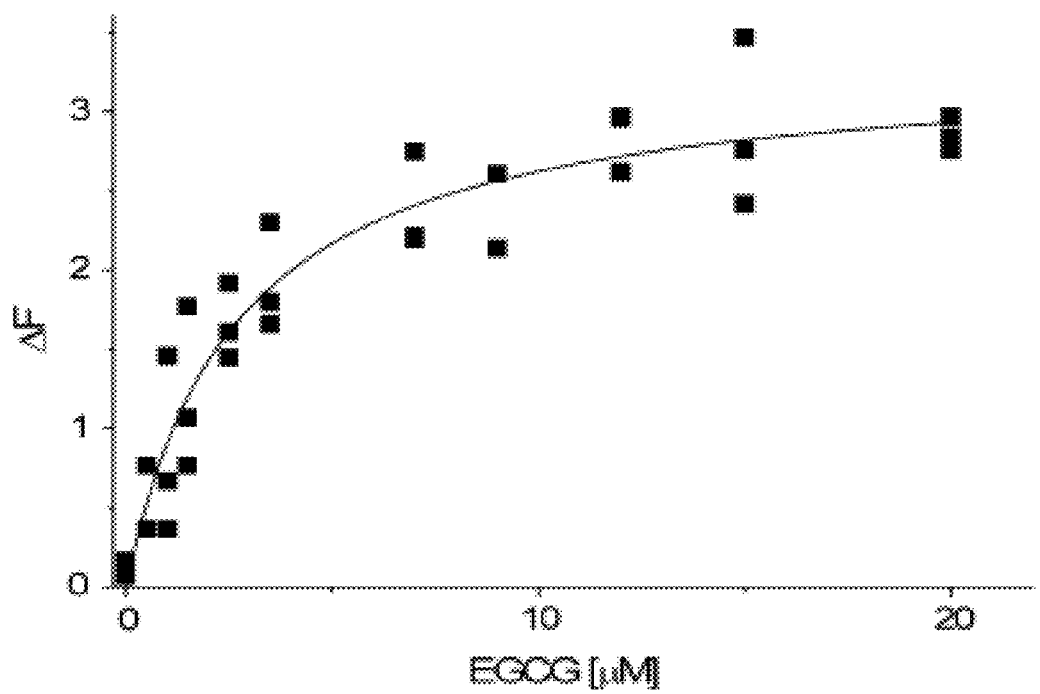
FIG. 5 demonstrates non-linear curve fitting to Langmuir-based model (Eq. 2) to the results of negative change ($F_0$–F) in fluorescence emission intensity of the protein with increasing EGCG concentration at pH=6.87.

The analysis for determination of the binding constants was performed using a Langmuir-based model, assuming one affinity-class of binding sites, as described by equation (2):

$$F_0 - F = \frac{(F_0 - F_\infty)L_0}{1/K_a + L_0} \tag{2}$$

where F and F0 are the fluorescence intensities of the protein solution in the presence and in the absence of the ligand, respectively; F∞ is the fluorescence when the protein is saturated with the ligand and $L_0$ is the total ligand concentration. The decrease in the fluorescence in the presence of different EGCG concentrations was recorded, and the association constant ($K_a$) as well as the value for maximum fluorescence difference ($\Delta F_{max} = F_0 - F_\infty$) were calculated by non-linear curve fitting to equation 2 (FIG. 5). The parameters for the fitting were based on the quenching of Tyr and Trp fluorescence at pH 6.87, for β-Lg concentration of 2 μM. The values obtained from the curve fitting to the Langmuir-based model were as follows: $R^2 = 0.89$, $\Delta F_{max} * 10^6 = 3.31 \pm 0.17$, $K_a = (3.7 \pm 0.67) * 10^{-5} M^{-1}$ where $\Delta F$ corresponds to the corrected difference between $F_0$ and F.

Table 1 summarizes the estimated $K_a$ values for the preheated and native β-Lg. At the excitation wavelength of 280 nm the $K_a$ for the preheated protein was significantly larger, indicating a better binding at the denatured state, while at the excitation of 295 nm the standard error intervals of the $K_a$ between the preheated and native (non-preheated, designated "RT") protein overlapped. At the excitation of 280 nm all six β-Lg fluorophores (4 tyrosines, 2 tryptophans) are excited while at 295 nm only the two Trp fluorophores are excited.

TABLE 1

Association constants ($K_a$) for binding of EGCG to β-Lg at different excitation wavelengths with (+) and without (−) heat treatment

| Excitation wavelength: | 280 nm | 295 nm | 280 nm | 295 nm |
|---|---|---|---|---|
| Preheating the protein solution (20 min., 75° C.) before adding EGCG | + | + | − | − |
| $K_a \pm$ S.E. ($10^5 M^{-1}$) | 3.7 ± 0.67 | 3.3 ± 1.07 | 1.05 ± 0.34 | 1.9 ± 0.6 |

A reason for the difference between the significance of the Ka at the excitation of 280 compared to the excitation of 295 nm might be the heating having a more distinct effect on exposing the surroundings of the 4 tyrosine amino acids for EGCG binding compared to the surroundings of the two tryptophans, or that the larger number of fluorophores gave a better signal to noise ratio. The association constants obtained were close to literature values for binding of different phenolic compounds to proteins.

Example 3

Evaluating Binding Constant by the Stern-Volmer Equation

Figure 6A:
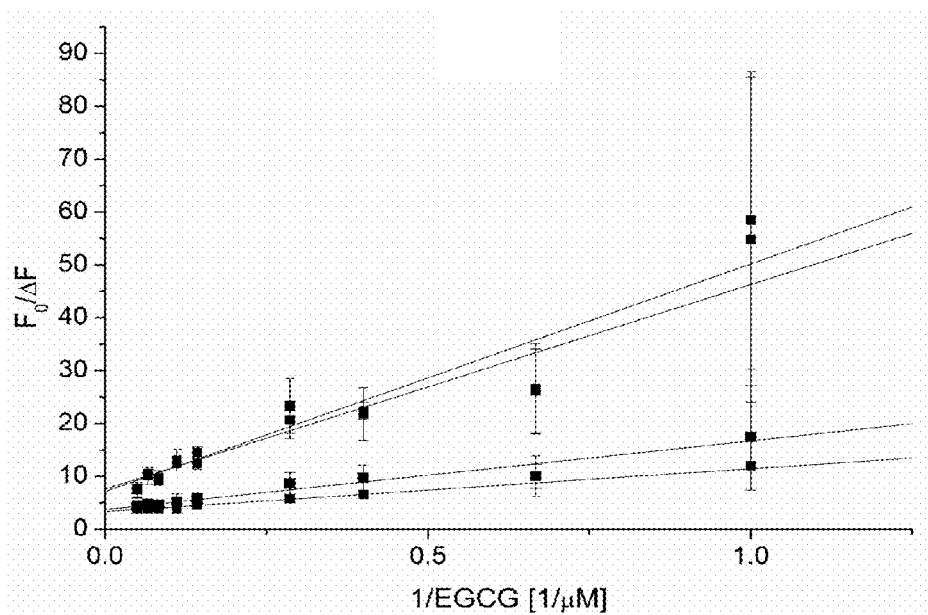
FIG. 6A presents modified Stern-Volmer plots of EGCG-β-Lg complexes at pH=6.86 with preheated β-Lg ($2 \times 10^{-6}$ M); excited at 280 nm (square) or 295 nm (circle) and with native protein excited at 280 nm (triangle) or at 295 nm (inverted triangle).
Figure 6B:
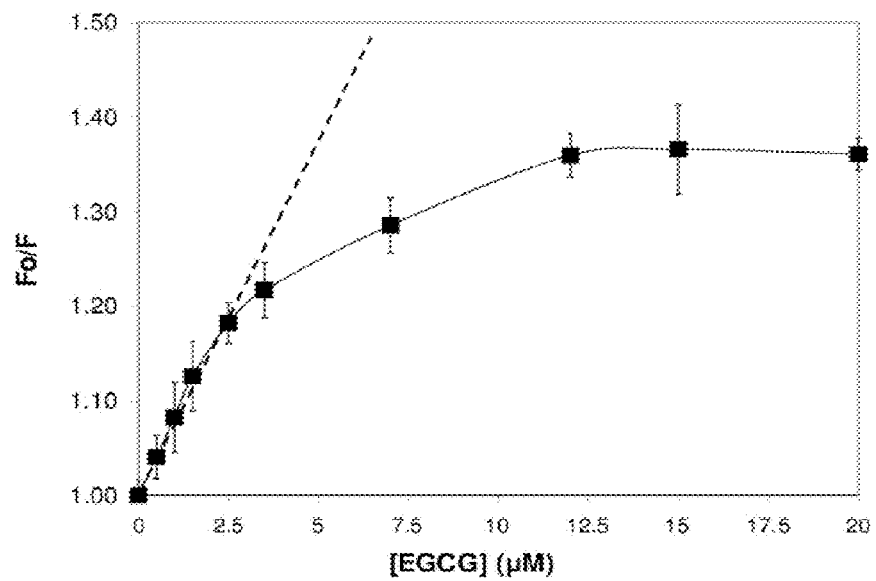
FIG. 6B shows Stern-Volmer plot of the quenching of preheated β-Lg by EGCG β-Lg concentration=$2 \times 10\text{-}6$ M; pH=6.86), and the corresponding linear correlation (dashed) where deviation from linearity indicates site-inaccessibility (error bars represent standard error).

Fluorescence quenching is often described by the Stern-Volmer equation (3):

$$\frac{F_0}{F} = 1 - K_{SV} * [Q] \tag{3}$$

where $F_0$ and F are the fluorescence intensities before and after the addition of the quencher, respectively, $K_{SV}$ is the Stern-Volmer quenching constant and [Q] is the concentration of the quencher. A linear Stern-Volmer plot is generally indicative of a single class of fluorophores, all equally accessible to the quencher. Without being bound to any theory or mechanism, it is speculated that a Stern-Volmer plot that curves towards the x-axis may indicate the existence of more than one fluorophore population, of which at least one population is not accessible to the quencher. This theory is logical in a globular protein of 6 fluorophores. As shown in FIG. 6B, the Stern-Volmer plot of the quenching of preheated β-Lg by EGCG (β-Lg concentration=$2*10^{-6}$M; pH 6.86) shows a significant shift from linearity, indicating the existence of a population of inaccessible fluorophores. The error bars in FIG. 6B represent standard error. The assessment of the fraction of fluorophore accessible to the quencher was performed using the modified Stern-Volmer equation (4):

$$\frac{F_0}{F_0 - F} = \frac{1}{f_a * K_{SVa} * [Q]} + \frac{1}{f_a} \tag{4}$$

where F and F0 are the corrected emission intensities of the protein solution in presence and in the absence of the ligand, respectively, $f_a$ is the fraction of fluorophore-sites accessible to the ligand, [Q] is the quencher (ligand) concentration, and $K_{SVa}$ is the Stern-Volmer quenching constant of the accessible fraction. This method has been used to study the binding of EGCG to human serum albumin (HSA) and to lysozyme. The modified Stern-Volmer plots of the various EGCG-β-Lg complexes are shown in FIG. 6A. The plot corresponds to EGCG-β-Lg complexes having β-Lg concentration of $2*10^{-6}$M, pH=6.86, preheated and excited at 280 nm (square) or at 295 nm (circle) and to the native protein excited at 280 nm (triangle) or at 295 nm (inverted triangle). From the intercept and slope of the linear trend line of $F_0/(F_0-F)$ vs. 1/[EGCG] plot $f_a$ and the $K_{SVa}$ were calculated (Table 2). The error bars in FIG. 6A represent standard error. The intercept represents the extrapolation to infinite quencher concentration (1/[Q]=0). The value of $F_0/(F_0-F)$ at this quencher concentration represents the reciprocal of the fluorescence intensity fraction that was quenched. At high quencher concentrations only the inaccessible residues would be fluorescent.

TABLE 2

Stern-Volmer quenching constants for binding EGCG to β-Lg

| Excitation wavelength: | 280 nm | 295 nm | 280 nm | 295 nm |
|---|---|---|---|---|
| With (+) or without (−; RT) preheating the protein solution for 20 minutes at 75° C. prior to EGCG addition | + | + | − (RT) | − (RT) |

TABLE 2-continued

Stern-Volmer quenching constants for binding EGCG to β-Lg

| Excitation wavelength: | 280 nm | 295 nm | 280 nm | 295 nm |
|---|---|---|---|---|
| $f_a$ ± S.E. | 0.32 ± 0.05 | 0.25 ± 0.07 | 0.16 ± 0.07 | 0.15 ± 0.06 |
| $K_{SVa}$ ± S.E. [$10^5 M^{-1}$] | 3.31 ± 0.7 | 3.07 ± 1.05 | 1.4 ± 0.7 | 1.4 ± 0.7 |

Similar values of accessible fluorophore were found at both excitation wavelengths, and the values of the accessible fraction of the heated protein sites were approximately twice compared to those found for the native protein. These results indicate that the heating partially exposed previously inaccessible sites on the protein, an expected outcome of protein unfolding. The Stern-Volmer quenching constants ($K_{SVa}$) obtained, which had been suggested to be very close to the binding constants were, in most cases, similar to the association constants displayed in Table 1. Overall the results indicate that heat-induced unfolding increased both the fraction of accessible binding sites, and the binding affinity, apparently due to exposure of hydrophobic domains which strengthened the hydrophobic interactions between EGCG and β-Lg. The more intimate contact facilitated by the unfolding and the hydrophobic interactions may assist the formation of H-bonds between oxygen-containing groups of EGCG and amides and other H-bonding groups of the protein, which should strengthen upon cooling.

Example 4

Particle Size Distribution Analysis of the Co-Assembled Nanoparticles

Dynamic light scattering was used to evaluate size distribution of the nanocomplexes formed, and that of the pure protein. To produce particles containing the EGCG: β-Lg molar ratios 2:1, 4:1, 6:1, 8:1 and 10:1, two experiments were performed:

(1) β-Lg solution (0.54 mM, in 0.9 ml of 30 mM PBS, pH 7) was heated to 75° C. for 20 minutes, and then EGCG solutions (1.96 mM-10.25 mM, in 0.48 ml of 5 mM PBS, pH 2.5) were added. The final EGCG concentrations were 0.65 mM-3.46 mM (0.03%-0.16%), the final β-Lg concentration was 0.35 mM (0.65%) and the pH of the final solution was 6.56.

(2) β-Lg (0.54 mM in 1.2 ml of 30 mM PBS, pH 7.1) was heated to 75° C. for 20 minutes, and EGCG solutions (4.36 mM-21.82 mM in 0.3 ml of 5 mM PBS pH 2.5) were added. The final EGCG concentrations were 0.87 mM-4.36 mM (0.04%-0.2%), the final β-Lg concentration was 0.43 mM (0.8%) and the pH of the final solution was 6.88.

After polyphenol addition, samples were vortexed for 20 seconds and allowed to cool to room temperature before measurement.

Figure 7:
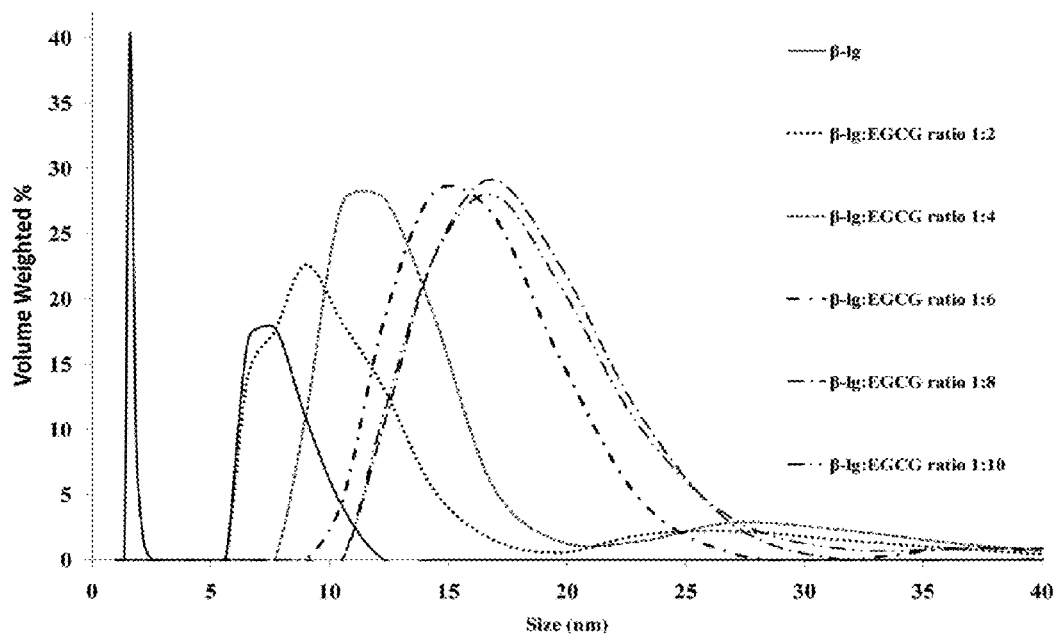
FIG. 7 exhibits the volume-weighted DLS size distributions of nanocomplexes of β-Lg (preheated for 20 min at 75° C. before EGCG addition) and EGCG at different β-Lg:EGCG molar ratios.

Particle size distribution was studied by a dynamic light scattering (DLS) analyzer (NICOMP™ 380, Particle Sizing Systems Inc., Santa Barbara, Calif., USA) equipped with an Avalanche Photo Diode (APD) detector, used at a fixed angle of 90°. The 90 mW laser wavelength was 658 nm. Mono- bi- or tri-modal distributions were calculated from the scattered light intensity fluctuations, by cumulants Nicomp™ analysis of the auto correlation function (see supplementary information in (Shapira, Assaraf, & Livney, 2009) for a more complete method description). The size range for the Nicomp distribution analysis was set to 1-1,000 nm. Measurements were made in duplicates at 25° C. Table 3 and FIG. 7 show an increase in particle size with increasing EGCG concentration indicating the formation of preheated complexes/nanoparticles (75° C., 20 min before EGCG addition). The molar ratios of β-Lg to EGCG presented in FIG. 7 are: 1:0 (straight line), 1:2 (dotted line), 1:4 (broken line), 1:6 (bold line/dot/line; -•-), 1:8 (fine line/dot/line; -•-) and 1:10 (line/2 dots; -••). The features characterizing the molar ratio curves of FIG. 7 are listed in Table 3.

TABLE 3

Characteristic sizes ($\bar{d}$) and volume-weighted fractions ($f_{vw}$) of the bimodal size distributions of β-Lg-EGCG nanoparticles at different molar ratios and pH values

| | β-Lg conc.: | | | | | | | |
|---|---|---|---|---|---|---|---|---|
| | 0.43 mM (0.8% (w/w) pH 6.88) | | | | 0.35 mM (0.65% (w/w) pH 6.88) | | | |
| | Peak[b]: | | | | | | | |
| | I (β-Lg) | | II (β-Lg-EGCG) | | I (β-Lg) | | II (β-Lg-EGCG) | |
| | β-Lg:EGCG | | | | | | | |
| molar ratio | $\bar{d}$ ± std (nm) | $f_{vw}$ (%) ± std | $\bar{d}$ ± std (nm) | $f_{vw}$ (%) ± std | $\bar{d}$ ± std (nm) | $f_{vw}$ (%) ± std | $\bar{d}$ ± std (nm) | $f_{vw}$ (%) ± std |
| 1:0 (Pure β-Lg) | 1.4 ± 0.0 | 99.8 ± 0.0 | 20.2 ± 0.0 | 0.2 ± 0.0 | 4.8 ± 3.1 | 99.6 ± 0.5 | — | — |
| 1:2 | 1.8 ± 0.0 | 98.5 ± 0.5 | 17.8 ± 1.2 | 1.5 ± 0.5 | 9.6 ± 1.7 | 92.8 ± 3.8 | 28.9 ± 2.1 | 7.0 ± 3.7 |
| 1:4 | 1.8 ± 0.2 | 96.8 ± 0.6 | 15.6 ± 0.5 | 3.2 ± 0.6 | 12.0 ± 0.6 | 96.2 ± 3.6 | 29.4[a] | 3.6 ± 3.6 |
| 1:6 | 2.1 ± 0.4 | 96.4 ± 2.1 | 17.6 ± 0.1 | 3.6 ± 2.1 | 15.7 ± 1.0 | 96.9 ± 2.5 | 82.2 ± 41.2 | 2.9 ± 2.6 |
| 1:8 | 2.6 ± 0.3 | 87.4 ± 3.3 | 18.9 ± 1.0 | 12.6 ± 3.2 | 17.2 ± 0.7 | 99.2 ± 0.9 | 70.5[a] | 0.7 ± 0.7 |
| 1:10 | 2.2 ± 0.3 | 89.8 ± 3.3 | 19.6 ± 0.1 | 10.2 ± 3.3 | 17.1 ± 0.4 | 99.8 ± 0.2 | 399.3[a] | 0.2[a] |

[a]In a few cases the second peak appeared only in one of the duplicates.
[b]Occasional third peaks were less than 0.4% and thus not reported.

As the size of the complexes was around 18 nm and that of the protein molecules around 2 nm (~9 times larger) the complexes may be roughly estimated ($9^3$=729) to contain several hundreds of β-LG and EGCG molecules. Table 3 also demonstrates the high pH-sensitivity of the co-assembly of EGCG and β-Lg.: the EGCG-β-LG particles formed at pH 6.56 are significantly larger than the particles formed at pH 6.88 even though the protein concentration at the latter pH was slightly higher. This observation might be attributed to the larger repulsion between the protein molecules at the higher pH. Additionally, the increase in EGCG concentration at pH 6.56 caused an increase in size of the smaller peak, while at pH 6.88 the increase in EGCG concentration caused a relatively small increase in the size of the smaller peak, but a large increase in the volume-based fraction of the larger peak. Furthermore, above a molar ratio of 1:8 there was almost no increase in the average particle size or distribution at both pH values. This saturation behavior is in accord with the data obtained from fluorescence measurements showing a plateau approximately at the same molar ratio (FIG. 3A).

The addition of EGCG to the heated protein solution caused an immediate appearance of cloudiness and formation of large visible fibrilar complexes. After 20 seconds of intensive vortexing the cloud unexpectedly disappeared and the systems became clear (See FIG. 8A), with nano sized particles as was concluded from the above DLS measurements. It is noteworthy that if only a brief vortexing was applied, visible strings of protein complexes remained in the solution, which did not dissolve with time, emphasizing the importance of the intensive shearing during mixing of the solutions, for the formation of the desired nano sized particles. This also suggests the possibility of using the shearing time and intensity as factors for controlling nanoparticles size and morphology. Overall, the sensitivity of the particle size to pH, shear and EGCG concentration facilitates the control of the physical properties of the nanocomplexes. However, it also suggests that in some cases the systems obtained might not be in thermodynamic equilibrium, and care should be taken to further study their colloidal stability with time for specific practical applications. Additionally, it is important to note that these complexes were prepared in simple model systems containing mostly water, protein and EGCG, and that the effect of other co-solutes like salts, sugars and other proteins, present in food products, might affect the nanoaggregates. Therefore, it would be advisable to test the performance of this technology within the actual product prior to application.

Example 4

Protection Against EGCG Oxidation

Figure 2A:
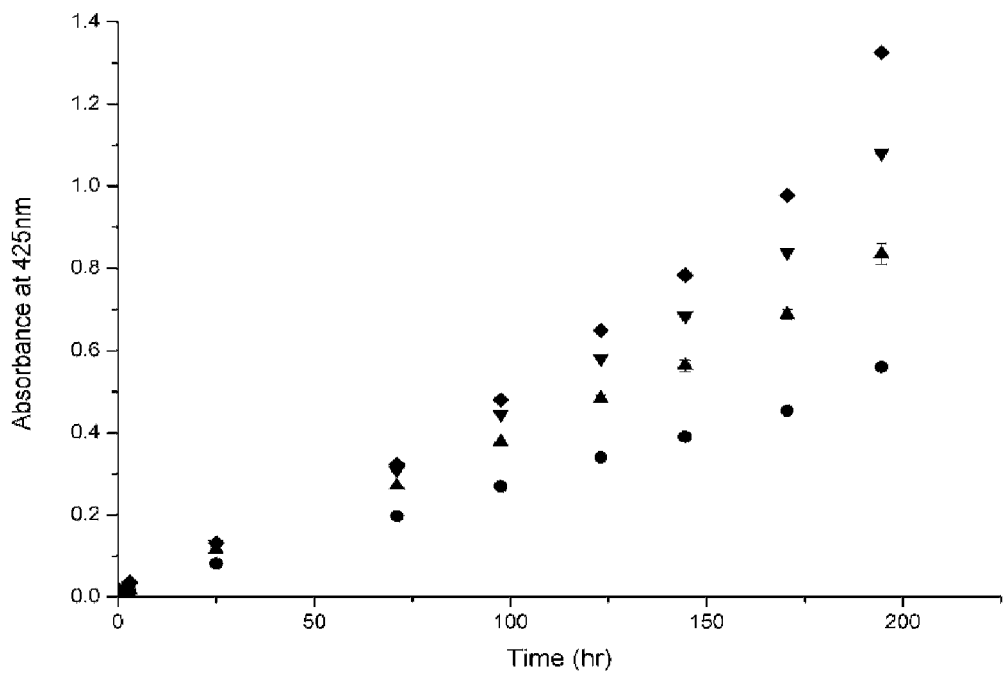
FIG. 2A shows absorbance at 425 nm of EGCG solutions of various EGCG concentrations (circle-0.05%; triangle-0.1%; upside down triangle-0.2%; diamond-0.5%) and as a function of time in 30 mM PBS, pH 6.8, as an indication of EGCG deterioration.
Figure 2B:
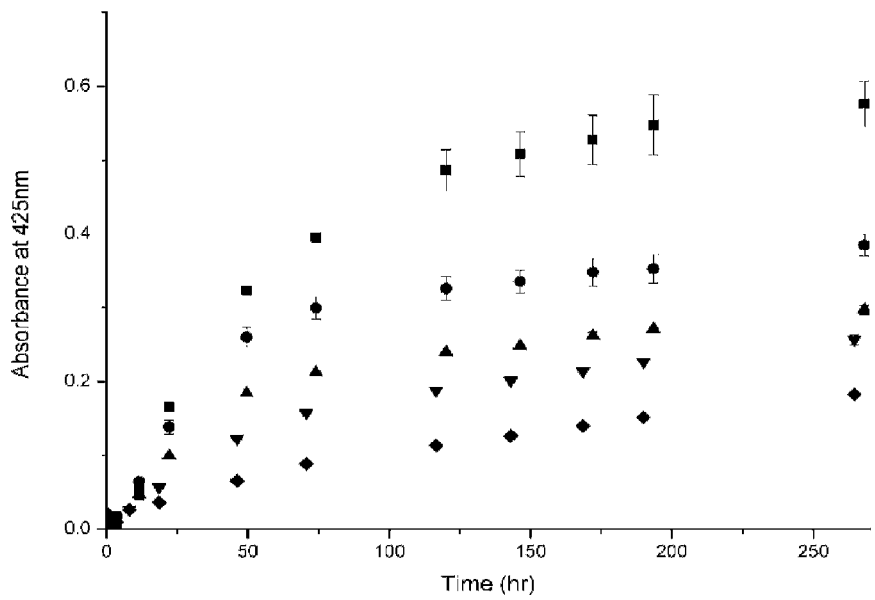
FIG. 2B exhibits absorbance at 425 nm of EGCG solutions in Aqua Nova® mineral water as a function of time and EGCG concentration: square—0.01%; circle—0.05%; triangle—0.1%; upside down triangle—0.2%; diamond—0.5%.

As the appearance of yellow color correlates with deterioration/oxidation of EGCG, the absorbance of solutions with different EGCG concentrations in mineral water (FIG. 2B) were monitored over time, to assess the need for protection of EGCG. FIG. 2 shows that in PBS pH 6.8, the degradation rate increased with rising EGCG concentration. There was no increase in the 425 nm absorbance of EGCG solution (0.05%) in a pH 2.5 PBS with time. This was in accord with literature data indicating higher stability of EGCG in acidic media. It is important to note that EGCG was reported to degrade even in the acidic Coca Cola® suggesting that pH alone cannot protect this molecule in complex food products. To evaluate the protection, conferred by complexation with β-Lg, against EGCG oxidation, the absorbance at 425 nm for 200 hours was tested, using visible-light spectrophotometry. Solutions of 0.52 mM (0.95%) protein at a 2:1 molar ratio (EGCG:protein) and pH 6.85 were compared to pure EGCG solutions. The protein was preheated at 2 temperatures (75° C. and 85° C.) for 20 minutes or kept at room temperature, to compare the protection provided by the partially denatured protein to that of the native protein. The reason for testing these two temperatures was that according to the literature, at about this pH, between 65-75° C. small proteins oligomers are formed, while between 75-85° C. some aggregation of the oligomers occurs.

The co-assemblies were prepared as described above, using 0.54 mM (1%) β-Lg in 1.9 ml 30 mM PBS pH 6.9, 75° C. or 85° C., for 20 min, and controls at room temperature. EGCG solution used was 21.82 mM (1%) in 0.1 ml of 30 mM PBS, pH 2.5. Appropriate controls of β-Lg without EGCG and EGCG without β-Lg at the respective concentrations and pH were performed. After preparation, the samples were placed in 1 cm path length spectrophotometer cuvettes and covered with parafilm. The final EGCG concentration was 1.09 mM (0.05%) the final β-Lg concentration was 0.52 mM (0.95%), and the molar ratio was ~2:1 (EGCG:β-Lg), and the pH of the final solution was 6.85.

Figure 8A:
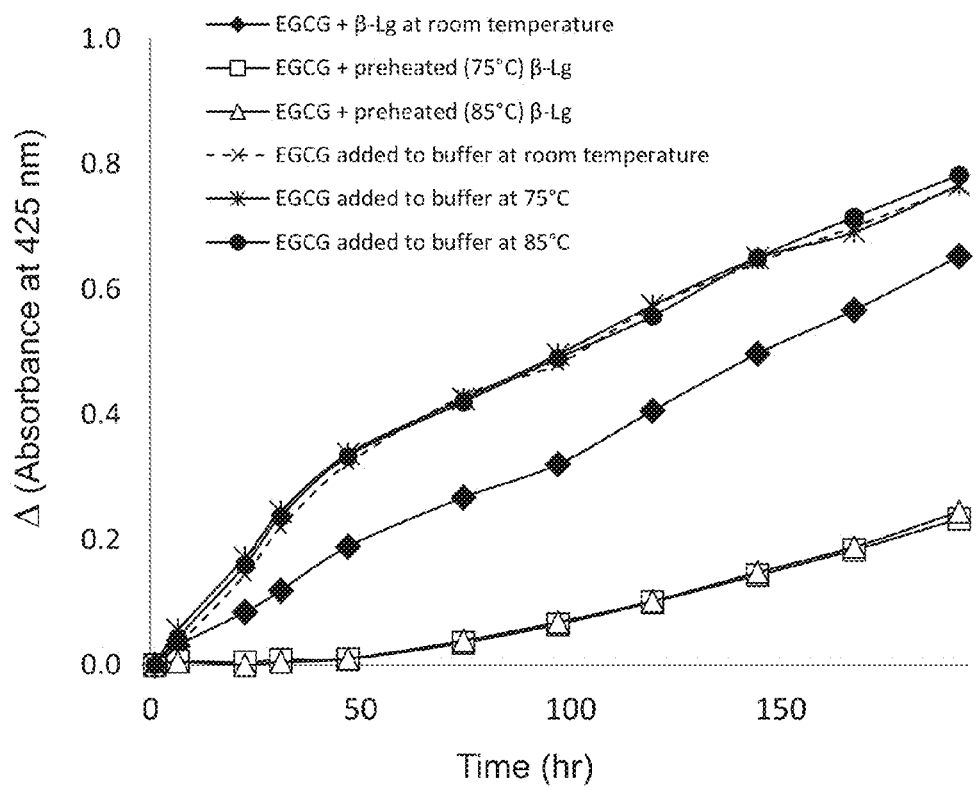
FIG. 8A shows the protective effect of the co-assemblies against EGCG deterioration monitored by the change in absorbance at 425 nm of EGCG alone or in a nanoparticle composition with β-Lg (error bars represent standard error).

As shown in FIG. 8A during the eight days of the experiment at room temperature, all the solutions showed an increase in the absorbance at 425 nm. Pure EGCG solution that was not protected by the protein showed the fastest increase in the absorbance, with no significant difference between EGCG added to buffer at room temperature or added to buffer that was preheated to the same temperature for the same time as the protein solutions.

When EGCG was added to native β-Lg there was only a mild decrease in the degradation rate. However, when the protein was preheated to 75° C. or 85° C. before mixing—in EGCG, a significantly slower degradation rate of the latter was observed, and for the first 48 hours there was practically no degradation observed (a time period of fastest degradation in the pure EGCG samples). No difference was seen between the two temperatures studied, 75 and 85° C.

Figure 8B:
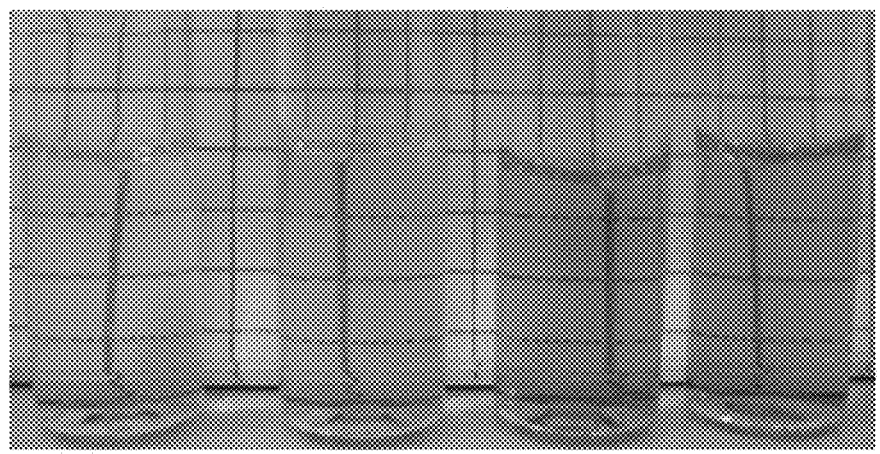
FIG. 8B is a photo of vials (duplicates) containing non denatured (A) and denatured (B)β-Lg with EGCG, 48 hours after preparation.

FIG. 8B (inset) is a photo taken after 48 hours showing the difference in color between the unprotected EGCG (vials 'B') and the EGCG in the preheated protein (85° C.) solution (vials 'A'). Vials 'A' contained heat treated nanoparticles comprising EGCG 1.09 mM (0.05%)—β-Lg 0.52 mM (0.95%) at pH 6.85 and 2:1 molar ratio. The heat treatment include heating the protein solution at 85° C. for 20 min. Vials 'B' contained EGCG 1.09 mM (0.05%) in PBS pH 6.85 buffer preheated at 85° C. for 20 min. Photos were taken 48 hours after preparation. The native protein provided some protection, and it is possible that this weaker protection is due to the weaker binding, and to the antioxidative nature of β-Lg. Similarly, the free sulfhydryl group of HSA was recently shown to act as an antioxidant for EGCG. When β-Lg was heated to 100° C. for 2 min, its antioxidative capacity declined, apparently due to oxidation of free thiol groups by oxygen and formation of disulfide bonds. However, the free thiol, Cys121, is known to be buried under the alpha helix in the native β-Lg. Upon mild heating, the alpha helix slightly unfolds, revealing Cys121 which consequently initiates the sulfhydryl-disulfide bond interchange chain reaction. Therefore, it is possible that mild heating (such as the heat treatments used in the current study), especially if the dissolved oxygen level is low due to a heat-induced degassing effect, may even improve the antioxidative capacity compared to the native protein. Without being bound to any theory or mechanism, it is speculated that the protection provided by the complexes may be further explained by an additional mechanism: by binding and entrapping EGCG in β-Lg complexes, it is immobilized and sterically shielded, which reduces its activity, and protects it from oxidizing agents.

Similar experiments were performed several times, at different temperatures from 75 to 85° C. and the results were consistent. However, an experiment, in which EGCG was added to the protein solution while it was still in the heating bath and left there at 75° for 20 minutes, showed a significant extent of yellow color formation during those 20 minutes, due to the fact that the high temperature significantly increases the degradation rate of EGCG. Therefore in designing the optimal procedure for this nano-entrapment process, it is desirable to keep the EGCG heat exposure to minimum, i.e. by fast cooling. Additionally an experiment was performed to test how the protection would change if the preheated protein is allowed to cool down before the addition of EGCG. The results indicated that the protection provided by this solution was almost the same as the protection provided by a protein that was not heated at all. This result also strongly implies that the preheating β-Lg, and mixing with EGCG while cooling, induces the formation of stronger, more numerous and consequently better protective co-assemblies compared to those formed with either native or with the preheated protein after its cooling to room temperature.

It is important to note that according to the growing body of literature on EGCG health effects, whose mechanisms are still not fully understood, the benefits revealed herein are probably not only due to the antioxidative properties of this compound. The complexation with β-Lg may lower the antioxidant properties of EGCG in the product as was previously found for EGCG with other milk proteins, caseins. However, it is hypothesized that upon proteolytic digestion, EGCG will be released, and its bioavailability and other desired properties will be consequently regained.

Example 5

Colloidal Stability

As detailed above, EGCG-β-Lg nanoparticles at neutral pH are smaller than 50 nm. In order to determine whether the addition of EGCG to the preheated β-Lg causes, in addition to a slight increase in size, a change in colloidal stability, different EGCG concentration solutions were added to the preheated β-Lg to create nano-complexes comprised of β-Lg:EGCG at molar ratios in the range of 1:0 to 1:8, while the β-Lg concentration remains constant at a neutral pH (6.8).

Figure 9A:
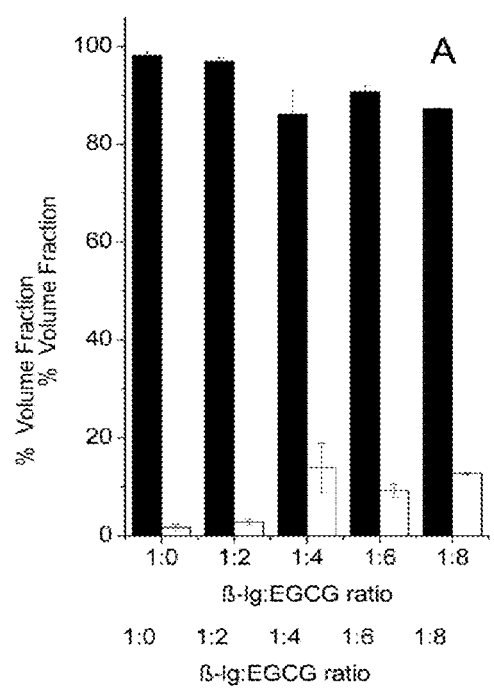
FIG. 9A shows the relative fraction sizes in the bimodal distributions of β-Lg-EGCG nanoparticles (black bar—small particles 1.5-3.5 nm, white bar—larger particles 11-23 nm) as a function of β-Lg:EGCG molar ratios.
Figure 9B:
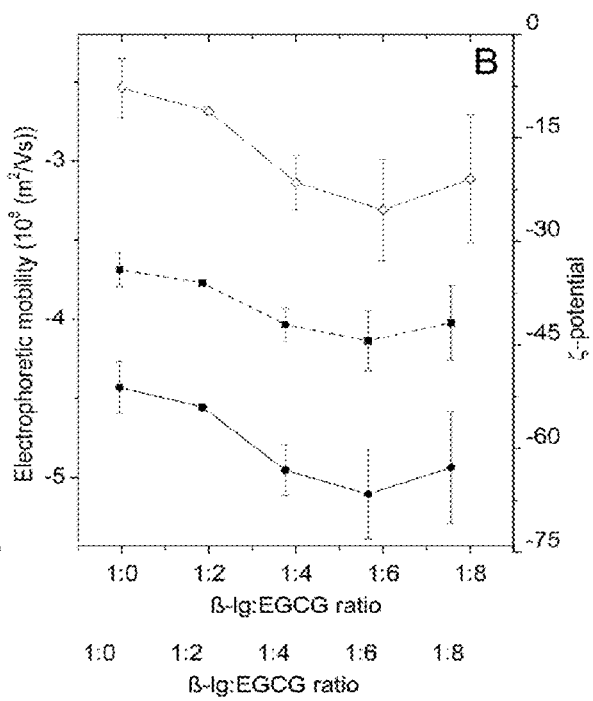
FIG. 9B exhibits electrophoretic mobility, measured under a 3 V/cm e-field at 25° C. (diamond) and zeta potential (Smoluchowski model—square, Huckel model—circle) of β-Lg-EGCG nanocomplexes as a function of β-Lg:EGCG molar ratios.

FIG. 9A shows the bimodal distributions of β-Lg-EGCG nanocomplexes at different β-Lg:EGCG molar ratios that were evaluated using dynamic light scattering. The size distribution of the nano-particles solution seemed to consist of two fractions. The first fraction included the small nano-particles in the range of 2-3 nm in diameter and the second fraction included nano-particles of about 15 nm. Since the size of the protein molecule is around 2 nm, it would be reasonable to assume that the smaller-size fraction represents unbound protein molecules or protein molecules with a few bound EGCG molecules, while the larger-size fraction represents complexes comprising several protein molecules, and probably also several EGCG molecules. Additionally it can be seen that as the EGCG concentration increased the volume-weighted percent of the larger-size fraction slightly increased. These results are similar to the results that were obtained previously (Shpigelman, et al., ibid). It was important to see whether the increase in the fraction of the larger sized complexes causes a decrease in colloidal stability. Therefore the predicted stability of the same complexes was studied by measuring the electrophoretic mobility (EM) of the nanocomplexes (FIG. 9B). For uniform and moderate electric fields, a linear relationship usually exists between the steady-state electrophoretic mobility and the zeta potential value (Delgado, et al. (2007) Journal of Colloid and Interface Science, Vol. 309, pages 194-224). The zeta potential is calculated according to the measured electrophoretic mobility using several theoretical models available. The choice of a suitable model is carried out according to the ratio of the particle radius (a) and the Debye length (κ-1) (i.e. a/κ-1=κ*a) which characterize the studied composition. The two commonly used models are the Smoluchowski model which is in use when κ*a is significantly larger than 1 (usually larger than 20) and the Hukel model which is in use when κ*a is smaller than 1. In the composition of the invention for the smaller particles (of ~2-3 nm) the κ*a was approximately 1.5. For the larger complexes of about 15 nm, the κ*a value was approximately 7.5. Since the ionic strength of the studied compositions was not high and the particle size (of the two fractions of particle sizes) was relatively small, the value of κ*a corresponds to the intermediate region, therefore, neither the Smoluchowski model nor the Hukel model strictly apply. In all cases, the Smoluchowski model, which gives the lowest absolute value zeta potential estimate for a given EM value among the commonly used models may be used as a conservative estimate. Particles having a sufficiently high electrostatic repulsion resist flocculation and their colloidal system would be stable (Zimet, et al., ibid). Suspension with zeta potential values more negative than −40 mV generally have good colloidal stability. The results shown in FIGS. 9A and 9B indicate that while the volume-weighted percent of the fraction of larger particles has increased as the EGCG concentration increased, the electrophoretic mobility of the system has not diminished in absolute value, but even became slightly more negative, suggesting better colloidal stability. While this may sound contradictory, in fact, at such small sizes there is no propensity to sediment, as the Brownian motion dominates. The very negative electrophoretic mobility may be conservatively translated to zeta potential values below −40 mV above 1:4 β-lg:EGCG molar ratio, which is a high stability regime. No significant change in the colloidal stability (as predicted from electrophoretic mobility) was seen as the EGCG:β-lg ratio increased from 4:1 to 8:1 (FIGS. 9A-B). The results indicate that despite the progressive complexation as the EGCG:β-lg ratio increases, the colloidal stability of the system is not compromised.

Without being bound by any theory or mechanism, it is suggested that the electrophoretic mobility of the nanoparticles is not adversely affected because EGCG probably binds the protein through hydrophobic interactions and hydrogen bonds, and because it is nonionic, it does not screen protein electrostatic charges by binding. Hence, the electrical repulsion between the nanoparticles is preserved and the colloidal stability of the composition of the invention is not diminished even with the increase of the EGCG concentration.

Example 6

Loading Efficiency and Loading Ratio of EGCG

The loading efficiency (the percentage of encapsulated substance out of total material added to the composition) and loading ratio (the ratio between the encapsulated substance and the encapsulation matrix) of EGCG was determined. β-Lg-EGCG nanoparticles solutions, of 2:1 and 8:1 EGCG:β-Lg molar ratios, were prepared at 1% w/w and 0.5% w/w protein solution. The entrapped EGCG in β-Lg nanoparticles was separated from the free EGCG by centrifugal ultrafiltration as described above. The molar loading ratio and the loading efficiency are presented on Table 4.

TABLE 4

Molar loading ratio and loading efficiency

|  | β-Lg 0.5% w/w | | β-Lg 1% w/w | |
| --- | --- | --- | --- | --- |
|  | Molar loading ratio | Loading efficiency (%) | Molar loading ratio | Loading efficiency (%) |
| EGCG: β-Lg 2:1 | 1.16 ± 0.04 | 58.5 ± 2.1 | 1.39 ± 0.04 | 71.0 ± 2.1 |
| EGCG: β-Lg 8:1 | 4.6 ± 0.6 | 58.6 ± 6.8 | 5.6 ± 0.1 | 70.0 ± 1.7 |

As shown in Table 4, the loading ratio increases with the increase of the β-Lg concentration in the composition and with the increase of the EGCG concentration in the composition. The loading efficiency and ratio were higher at β-Lg concentration of 1% w/w compared to their values at 0.5%. The increase in efficiency and ratio with increasing protein concentration may be attributed to the larger chance of EGCG and β-Lg to encounter during the formation of the complexes. This observation may be also attributed to a cooperativity effect, namely, a few protein molecules complexed together more easily entrap a larger number of EGCG molecules. This propensity may increase with increasing protein concentration. To test whether these results are not an artifact due to formation of a "filtration cake" that serves as a physical barrier to the EGCG during the filtration stage, similar experiment was performed using a molecule that has no known interaction with β-Lg, caffeine. The results did not show any binding or entrapment of caffeine in both β-Lg concentrations. It is therefore concluded that using the encapsulation method of the invention, relatively high loading efficiency, of about 70% in a composition containing 1% protein, is obtained given the fact that EGCG is water soluble.

As EGCG easily oxidizes, it is important to aim for maximal loading efficiency of the unprotected EGCG thereby minimize the amount of free EGCG in the system. For this purpose, the preferable molar ratio of EGCG to β-Lg is higher than 2:1, preferably within the range of 3:1 to 10:1, for example, about 8:1. This range of molar ratio provides maximal weight-based loading capacity of 12% (i.e. 12% EGCG in the particles), which is significantly better than the chitosan-tripolyphosphate-EGCG nanoparticles (0.37%) known in the art, and is within the range of the loading capacity of encapsulated punicalagin (a polyphenol derived from pomegranate) in gelatin (14.8-25.7%).

Example 7

Freeze-Drying and Reconstitution

Dried nanoparticles are easily stored and transported. Thus, using the nanoparticles of the invention in a dried form is an enormous advantage for utility in the food industry. The structure of the nanoparticles of the invention was studied after freeze-drying cycles using attenuated total reflectance Fourier transform infrared spectroscopy (ATR-FTIR) and the size of the reconstituted products was evaluated using dynamic light scattering (DLS).

Figure 10:
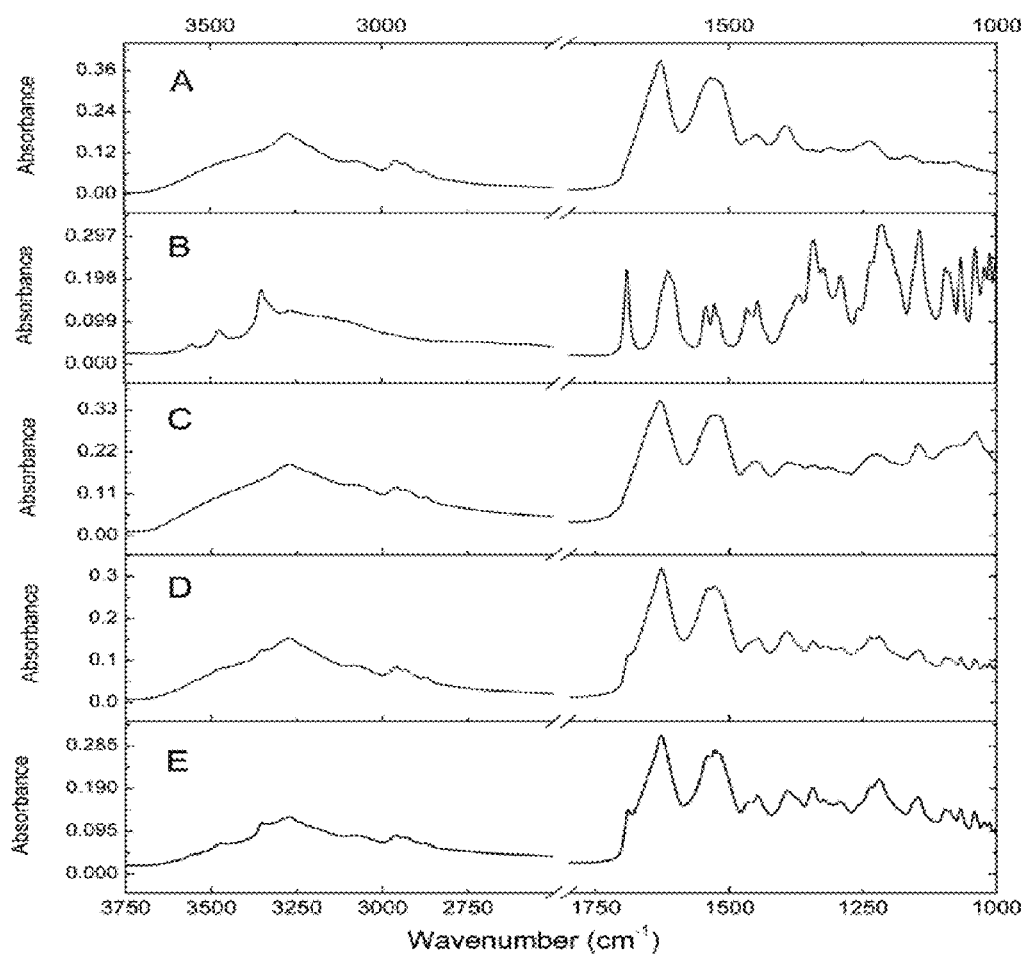
FIG. 10 presents ATR-FTIR spectra of dry samples of β-lg (A), EGCG (B), freeze-dried β-lg-EGCG nanoparticles, 1:8 molar ratio (C), β-lg-EGCG physical mixture, 1:8 molar ratio (D) and a mathematical summation of absorbance relative to the 1:8 β-lg-EGCG molar ratio.

The EGCG-β-lg nanoparticles were studied after freeze drying using ATR-FTIR to assess the binding interactions forming the complex in the powder form. The FTIR spectrum of the complex was compared to the spectrum of the physical mixture and to those of the pure substances. FIGS. 10A and 10B show the absorbance spectra of pure "empty" β-lg nanoparticles and pure EGCG, respectively. FIG. 10C shows the absorbance spectra of the dry nanoparticles and FIG. 10D shows the mathematical summation of the spectra shown in FIGS. 10A and 10B taking into account the appropriate EGCG and β-lg concentrations in the complexes. FIG. 10E is the spectrum of the physical mixture of the same EGCG and β-lg concentrations as in the complexes. One can easily see that while the physical mixture FIG. 10E and mathematical summation FIG. 10D exhibit a similar pattern, the nanoparticles (FIG. 10C) show a different pattern than the physical mixture, a pattern which is more similar to that of the protein (FIG. 10A) that underwent an identical process only without the addition of EGCG. For example in FIGS. 10D and 10E a small peak around 1690 $cm^{-1}$ is observed that also appears in EGCG powder (FIG. 10B). That peak may stand for the carbonyl stretching of the gallic acid. This peak is not detected in the spectra of the complexes. Similarly, a typical EGCG peak is shown around 3350 $cm^{-1}$ in the physical mixture and the mathematical summation, and is probably due to OH stretch of phenolic hydroxyl group. This peak is not detected in the nanocomplexes. Another observation distinguishing the various spectra is in the region of 1000-1200 $cm^{-1}$. The pure protein spectra had no peaks in this region, and in the physical mixture and the mathematical summation small peaks from the EGCG appear. However, in the complexes spectra a strong and broad band is easily observed. The bands in the 1000-1200 $cm^{-1}$ region may be attributed to vibrations of aromatic groups. Changes in the characteristic bands of pure substances confirm the existence of the complex as a new compound with different spectroscopic bands and the disappearance of peaks due to complex formation was shown to relate with formation of inclusion complexes of rosmarinic acid in cyclodextrins. It is noted that each spectrum shown in FIG. 10 is the average of 3 replicate experiments.

Some conclusions about the structure of the dried nanoparticles can be derived from the FTIR. A slight broadening of the peak around 3275 $cm^{-1}$ relating to intermolecular H-bonded and O—H stretching modes in the complexes compared to the pure protein is an indication of hydrogen bonds between EGCG and the protein. This observation is in agreement with previous findings suggesting that polyphenols bind to the protein partially using H-bonds. The amide I maxima of the β-lg was detected at 1627.1 $cm^{-1}$ similar to that previously shown for lyophilized β-lg (1628 $cm^{-1}$; Gosal, et al. (2002) Langmuir, Vol. 18, pages 7174-7181). While the mathematical summation and physical mixture of the protein showed a slight red shift or no shift at all of this band (1626.5 $cm^{-1}$ and 1627.1 $cm^{-1}$, respectively), the complex formation resulted in a blue shift of almost 2 $cm^{-1}$ (1629 $cm^{-1}$). This shift cannot be easily explained by the contribution of EGCG to the absorbance as it would have resulted in a blue shift also in the mathematical summation and physical mixture. Additionally the area around 1630 $cm^{-1}$ is not located in the maximal absorbance region of the EGCG. Although a previous study suggested that flavonoids did not affect the secondary structure of BSA upon binding the addition of the flavonol morin was shown to induce changes in the secondary structure of HSA. Additionally a result that showed a shift to higher wave numbers with addition of catechins to β-lg was previously shown upon addition of EGC was added to β-lg. In the deconvoluted spectra of β-lg, β-sheet conformation is assigned at 1624-1637 $cm^{-1}$ while the band of random coil and α-helixes are assigned to 1654±2.6 $cm^{-1}$ and 1645±1.5 $cm^{-1}$, respectively. Thus, the shift to 1629 $cm^{-1}$ may be attributed to the formation of a more random secondary structure of the protein.

Figure 11:
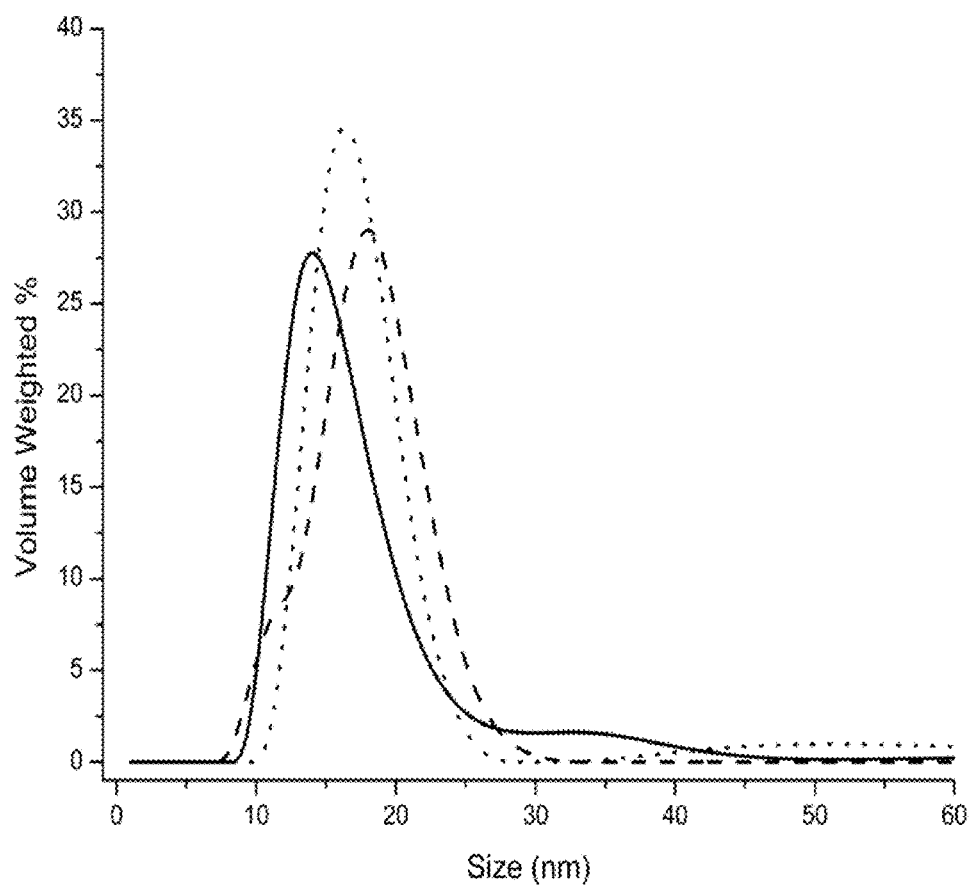
FIG. 11 shows the average (n=3) volume weighted percentage DLS size distributions of β-Lg and EGCG nanocomplexes before (solid line) and after freeze drying and reconstitution with HPLC grade water samples quenched frozen using liquid nitrogen (dashed line) or samples that were slowly frozen at −20° C. (dotted line).

The reconstitution of freeze dried nanoparticles is an important step for practical application. Freeze drying may induce aggregation or irreversible fusion of nanoparticles and thus the effect of freeze-drying on particle size was tested. As shown in FIG. 11 slow and fast freezing had an insignificant impact on the size distribution of the particles after reconstitution in water. The pH was 6.6 before and after the reconstitution. The measured sizes were 15.19±1.4, 18.18±1.68, 17.13±0.89 for the particles before freeze-drying and reconstitution, after quench freezing, freeze-drying and reconstitution, and after slow freezing, freeze-drying and reconstitution, respectively (points were connected with smooth lines by B-spline curve fitting (OriginLab 8.0)). The size of the particles after freeze-drying and reconstitution is small, thereby rendering the nanoparticles suitable for the preparation of clear solutions. Surprisingly, the freeze-drying process resulted with significantly improved dissolution rate of β-Lg compared to non-freeze-dried protein ((i.e. spray dried, as provided by the supplier)). In addition, a composition containing up to 1.6% β-Lg-EGCG freeze-dried nanoparticles dissolved in a few seconds under constant stirring.

Example 8

Sensory Evaluation

Figure 12:
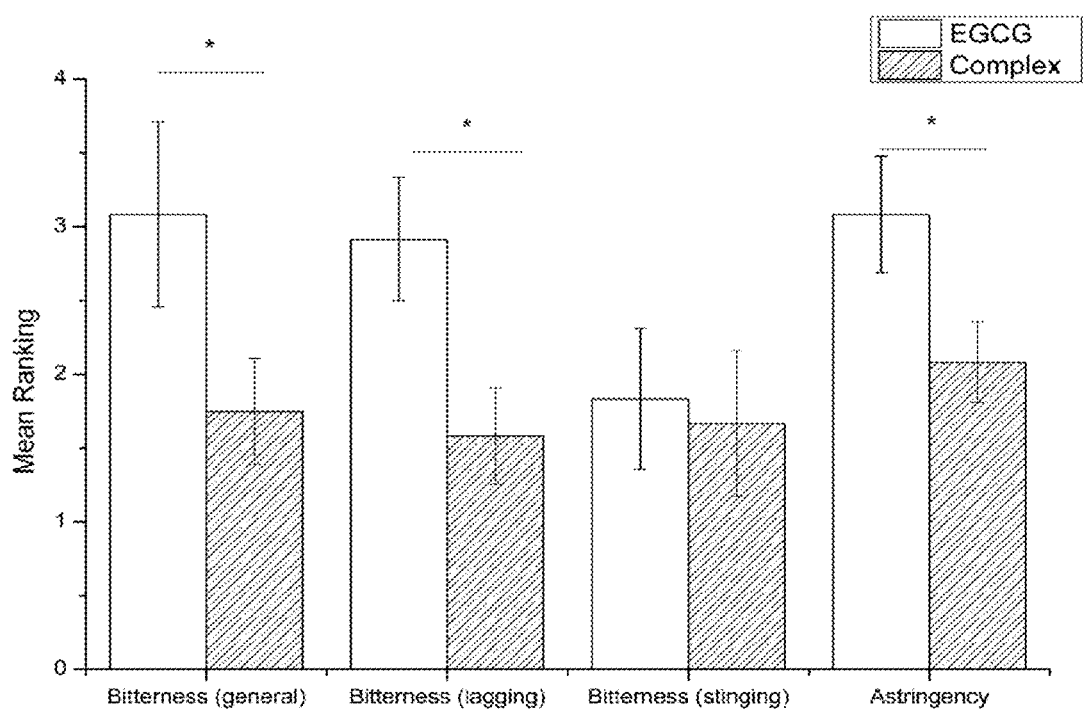
FIG. 12 exhibits bitterness and astringency ranking provided by a panel of tasters (n=6) for free EGCG and EGCG nanoparticles using a scale of 1 to 5 which stands for not detectable (1), faintly detectable (2), detectable (3), clearly detectable (4) and unpleasantly detectable (5), where significant differences ($P<0.05$) are designated with an asterisk.

Sensorial effect of encapsulating EGCG according to the invention after a scaled up process that included preparation of larger batched of nanoparticle solutions (about 10 L total in 0.25 L batches), freeze drying and reconstitution was evaluated by a professional sensory panel from Wacker Biosolutions (Wacker Chemie AG, Burghausen, Germany). The results are summarized in FIG. 12. The results show that the nanoencapsulated EGCG was less bitter (both in terms of general and lagging bitterness) and less astringent compared to an equal concentration of non-encapsulated EGCG.

Without being bound by any theory or mechanism, it is postulated that the beneficial sensory effect of the encapsulation results from the binding. The bound EGCG is less likely to interact with the bitter taste receptors and is less likely to interact with the salivary proteins, an interaction which results in astringency.

Example 9

Simulated Gastric Digestion

Simulated gastric digestion was performed at pH=2 and 37° C. under continuous shaking for different time periods, with pepsin, a gastric proteolytic digestion enzyme. The simulation reaction was terminated by adding 1M NaOH to pH to 6.6 (at pH above 6 pepsin is irreversibly inactivated) and followed by quench freezing using liquid nitrogen. Protein digestion in the system was analyzed by SDS-PAGE gels. The release of the EGCG was studied using membrane filtration followed by RP-HPLC analysis.

The optimal β-Lg/pepsin w/w ratio for the artificial digestion system was determined by digesting the nanoparticles (2:1 EGCG:β-Lg molar ratio) for 2 hours in different ratios of β-Lg/pepsin (from 100:1 to 5:1), while constantly shaking. The following samples were analyzed on SDS PAGE gel (FIG. 13): lanes 1 to 5—β-Lg/pepsin w/w ratio of 5, 10, 20, 50 and 100, respectively; lane 6 for no pepsin at pH 2; lane 7 for no pepsin without changing the pH, lane 8 for size markers (3.5 (weak band), 6.5, 14.4, 16.9, and 26.6 kDa); lane 9 for pepsin at pH 2.2, digestion time of 2 hours; and lane 10 for pepsin at pH 2.2, digestion time=0. The bands on the SDS PAGE gel (FIG. 13) were quantified into extent (percent) of digestion (Table 5).

TABLE 5

Band density (lanes 1-6 of FIG. 13) representing β-Lg - EGCG nanoparticles under simulated gastric digestion as a function of β-Lg/pepsin ratio

| β-Lg/pepsin ratio [% wt] | Intensity | % of initial intensity |
| --- | --- | --- |
| No pepsin | 61248 | 100 |
| 5 | 34453 | 56 |
| 10 | 45117 | 74 |
| 20 | 46475 | 76 |
| 50 | 50945 | 83 |
| 100 | 54673 | 89 |

A band representing the pepsin (MW=35 KDa) having a molecular weight above 26.6 KDa appeared in all lanes. Lanes 9 and 10 that represent the auto-digestion of the pure pepsin solutions showed two additional very weak bands having molecular weight of approximately 20 KDa. It may be that these bands correspond to pepsin autolysis products. Comparing lanes 1-5 in FIG. 13 with lanes 6-7, it seems that in the lanes that represent the β-Lg-EGCG nanoparticles which were not subjected to the proteolytic enzyme, two additional bands above 26.6 KDa (and also above 35 KDa, representing the pepsin) appeared. These bands may correspond to covalent conjugates composed of a few β-Lg molecules, with or without EGCG, attached together by disulfide bonds (if the amount of mercaptoethanol was insufficient to break them down during the SDS-mercaptoethanol heat treatment). Alternatively, it may be possible that covalent bonds form between β-Lg and EGCG, as has been suggested in the literature (Ishii, et al. (2011) Biosci Biotechnol Biochem, Vol. 75, pages 100-106; Mori, et al. (2010) Biosci. Biotechnol. Biochem., Vol. 74, pages 2451-2456) and these bonds may not break by mercaptoethanol. These conjugates were digested even at the lowest pepsin concentrations. Additionally a relatively small band of around 14.4 KDa appeared in lanes 6 and 7 that was also digested even at the lowest pepsin concentration. This band is probably representative traces of α-Lactalbumin (14.1 KDa; a common whey protein) contained in commercial batches of β-Lg, used to increase its relevance for the food industry.

Figure 13:
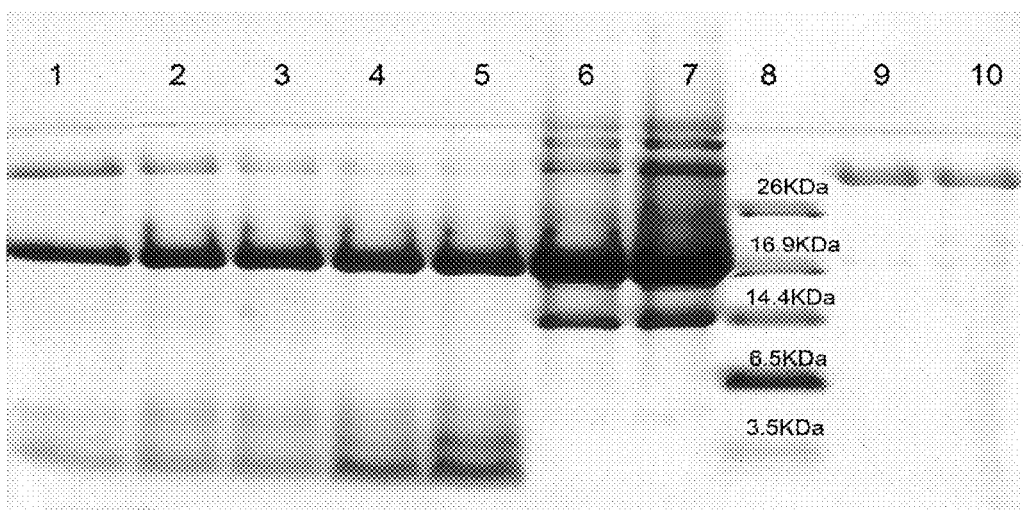
FIG. 13 exhibits SDS PAGE of nanoparticles (2:1 EGCG:β-Lg molar ratio) incubated with various ratios of β-Lg/pepsin (w/w).

According to lanes 1-5 in FIG. 13 β-Lg degraded faster with increasing pepsin concentration. Furthermore, as the pepsin concentration increased the resulting peptides became shorter and the intensity of the bands which represent the short peptides became weaker. The results further indicate that complete degradation of β-Lg is never achieved, not in any of the β-Lg/pepsin w/w ratios that were examined. The results are consistent with previous knowledge that β-Lg is resistant to physiological gastric digestion, and degrades only in the presence of a gross excess of pepsin (~13:1 pepsin to protein ratio, w/w).

To test protein degradation with time gastric digestion was examined by using β-Lg/pepsin w/w ratio of 20:1 under various digestion times, up to 3 hours. SDS PAGE (FIG. 14) was applied on the following samples: lane 1—EGCG solution (0.5 mg/ml), 120 min; lane 2—nanoparticles of β-Lg alone, 0 min; lane 3—nanoparticles made only of β-Lg, 120 min; lane 4—β-Lg-EGCG nanoparticles, 180 min; lane 5—size markers; lane 6—β-Lg-EGCG nanoparticles, 120 min; lane 7—β-Lg-EGCG nanoparticles, 90 min; lane 8—β-Lg-EGCG nanoparticles, 60 min; lane 9—β-Lg-EGCG nanoparticles, 30 min; and lane 10, β-Lg-EGCG nanoparticles, 0 min. The size markers (FIG. 14, lane 6) included bands which correspond to the following weights (kDa): 1.5 (very weak band), 3.5 (weak band), 6.5, 14.4, 16.9 and 26.6.

Figure 14:
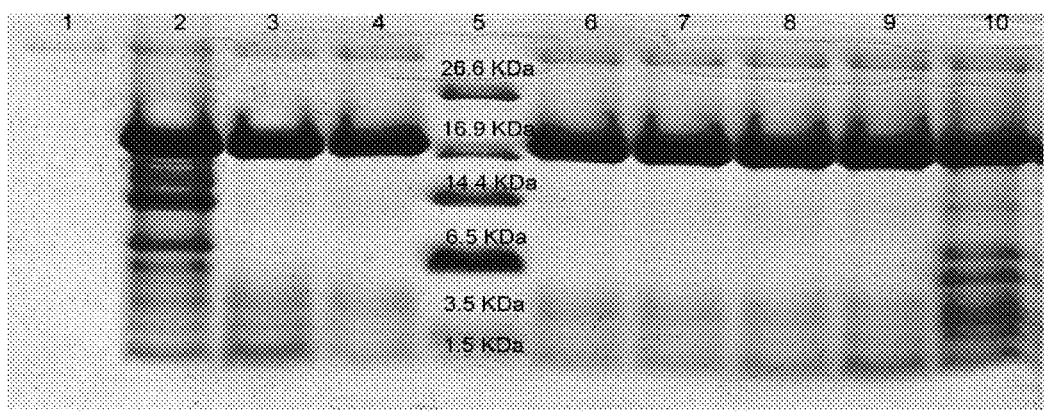
FIG. 14 presents SDS PAGE of nanoparticles (2:1 EGCG:β-Lg molar ratio) incubated with pepsin for different time periods.
Figure 15:
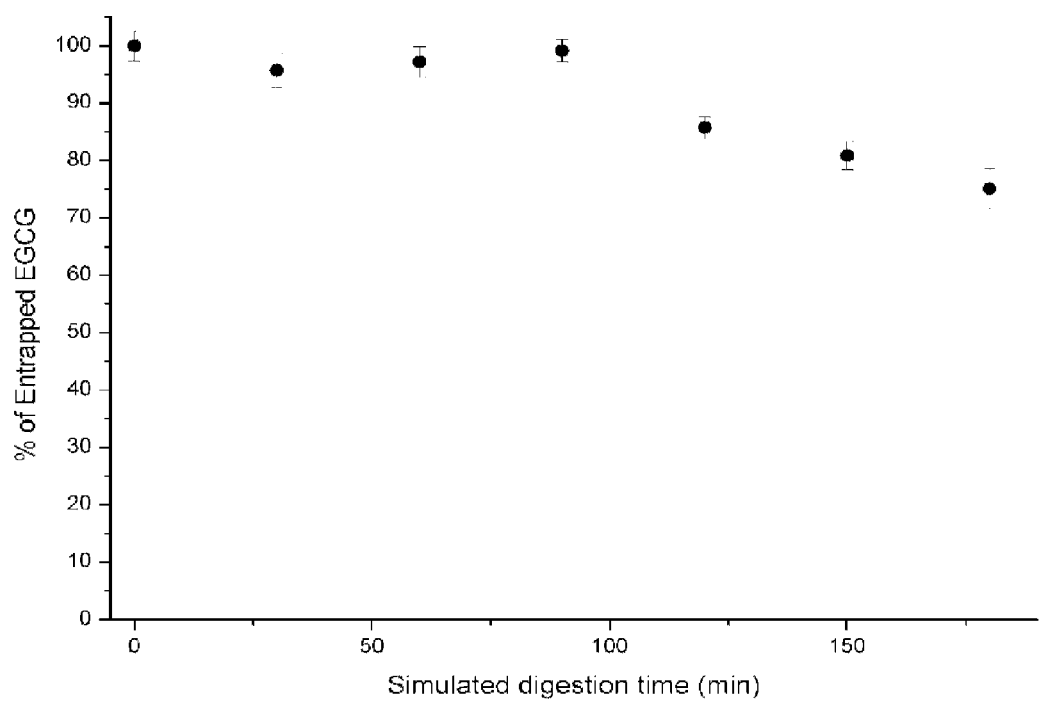
FIG. 15 shows the amount of EGCG remaining entrapped as percentage of the initially entrapped EGCG, as a function of time during digestion of β-Lg-EGCG nanoparticles under simulated gastric conditions.

Aliquots were taken every 30 minutes for both SDS-PAGE (FIG. 14) and for studying the EGCG release during 3 hours of digestion (FIG. 15). It is noted that lane 1 in FIG. 14, which presents digestion products of EGCG solution (final concentration of 0.5 mg/ml) without β-Lg, exhibits only one band above 26.6 KDa, representing pepsin. It is therefore assumed that EGCG is not stained by the coomassie brilliant blue. As expected FIG. 14 shows that the β-Lg band diminished with increasing digestion time and short β-Lg peptides appeared. Furthermore, as the digestion time increased the peptides became shorter. The color density analysis of the β-Lg bands from FIG. 14 is provided in Table 6. The color density diminishes as the simulated digestion continues and after 3 hours the color density of the band was 68% relative to the band at t=0.

TABLE 6

Band density (lanes 4-10 & lane 2-3 of FIG. 14) representing β-Lg - EGCG nanoparticles under simulated gastric digestion as a function of digestion time

| Digestion time (min.) | Intensity | % of initial intensity |
|---|---|---|
| 0 | 72216 | 100 |
| 30 | 65749 | 91 |
| 60 | 64681 | 90 |
| 90 | 61615 | 85 |
| 120 | 56780 | 79 |
| 180 | 49315 | 68 |
| 0 (without EGCG) | 68132 | 100 |
| 120 (without EGCG) | 51670 | 76 |

To study protein digestion relative to EGCG release from the nano-complexes, free EGCG was separated from the entrapped EGCG using centrifugal membrane filtration and concentration of the former was determined using RP-HPLC (FIG. 15). For 90 min. release of entrapped EGCG was not detected, while after 90 min. significant release of EGCG commenced, continuing for the following 90 min. The percent of released EGCG (of the initially entrapped EGCG) after 180 min. (25%) was similar to the percent of the digested β-Lg observed in the SDS PAGE analysis (32%) after the same period of time. The initial plateau in the release of EGCG seen in FIG. 15, compared to the visible digestion of the protein in the SDS PAGE during the first 90 minutes may be due to the fact that the filter used for separating free EGCG from encapsulated EGCG has 3 KDa pores. Therefore digested β-Lg peptides larger than 3 KDa could not pass through the filter and the EGCG attached to them was considered entrapped. After 90 minutes the system included a significant amount of peptides of less than 3 KDa which could pass through the filter, may or may not release the EGCG, but in any event would be considered as free (both experimentally, and practically-as a small peptide would provide little or no protection, and the binding would tend to be reversible). The combined results from the SDS PAGE and the digestive release measurements clearly show that there is very little release of the EGCG during gastric digestion and thus the nano-complexes of the invention provide an effective vehicle for the delivery of EGCG and possible also other polyphenols to the small intestine.

On one hand it was suggested that polyphenols might inhibit digestive enzymes and reduce food digestibility due to strong complexing abilities of the polyphenols with the digestive enzymes resulting in the change of enzyme molecular conformation leading to loss of catalytic activity. On the other hand, it was previously shown that EGCG is capable of increasing the initial velocity of the digestion reaction (Tagliazucchi, et al. (2005) Journal of Agricultural and Food Chemistry, Vol. 53, pages 8706-8713). Comparing lanes 2 and 3 in FIG. 14, which present heat treated β-Lg alone with lanes 10 and 6 which present the nanoparticles at digestion times of 0 and 120 min, respectively, it is shown that for all samples, the percentages of digested protein are very similar (Table 6: 79% to 76%). Therefore we can conclude that in the case of EGCG nanoparticles no significant effect on the activity of pepsin was noted.

Without being bound by any mechanism, the observation of relatively low digestion of β-lg may be attributed to the known resistance of β-Lg to physiological gastric conditions. Complete β-Lg digestion was not observed herein for any of the β-Lg/pepsin w/w ratios examined, including at 180 minutes of digestion, which is longer than the maximal normal gastric digestion time (120 minutes).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A clear liquid composition, comprising a plurality of nanoparticles, each nanoparticle consisting of denatured β-lactoglobulin and at least one nutraceutical compound selected from the group consisting of a polyphenol, a catechin, EGCG, EGC, EC and ECG, said composition having turbidity below 0.4.

2. The clear liquid composition of claim 1, wherein the plurality of nanoparticles exhibit a volume weighted average particle size lower than 100 nm.

3. The clear liquid composition of claim 1, wherein the plurality of nanoparticles exhibit a volume-weighted average particle size lower than 50 nm.

4. The clear liquid composition of claim 1, having a pH higher than 6.8.

5. The clear liquid composition of claim 1, wherein the molar ratio β-lactoglobulin to the at least one nutraceutical compound is within the range of 1:1 to 1:20.

6. The clear liquid composition of claim 1, having turbidity within the range of 0 to 0.1.

7. The clear liquid composition of claim 1, further comprising at least one agent selected from the group consisting of: vitamins, minerals, amino-acids, antioxidants, enzymes, hormones, botanicals, herbals, dietary supplements, pre-biotics, soluble fibers and energy sources.

8. A pharmaceutical composition, comprising the clear liquid composition of claim 1 wherein the liquid carrier is a pharmaceutically acceptable carrier.

9. The pharmaceutical composition of claim 8, further comprising at least one pharmaceutical agent.

10. The pharmaceutical composition of claim 8, wherein the plurality of nanoparticles is enclosed within the pharmaceutically acceptable carrier.

11. The pharmaceutical composition of claim 8 wherein the at least one nutraceutical compound is EGCG.

12. A method of preparing the nanoparticle composition of claim 1 comprising: a) providing a protein solution comprising β-lactoglobulin; b) providing a nutraceutical solution comprising at least one nutraceutical compound selected from the group consisting of a polyphenol, a catechin, EGCG, ECG, EGC and EC; c) incubating the protein solution at a temperature within the range of 65° C. to 99° C. thereby obtaining denatured β-lactoglobulin; and d) mixing the nutraceutical solution into the protein solution of (c), thereby obtaining said nanoparticle composition.

13. The method of claim 12, wherein the protein solution is incubated for 1 to 45 min.

\* \* \* \* \*